(12) United States Patent
Pasricha et al.

(10) Patent No.: US 8,669,258 B2
(45) Date of Patent: Mar. 11, 2014

(54) TREATMENT FOR GASTROPARESIS USING SEPIAPTERIN

(75) Inventors: Pankaj J. Pasricha, Cupertino, CA (US); Pandu R. R. Gangula, Nolensville, TN (US)

(73) Assignee: The Board of Regents of the University of Texas System, Austin, TX (US)

( * ) Notice: Subject to any disclaimer, the term of this patent is extended or adjusted under 35 U.S.C. 154(b) by 278 days.

(21) Appl. No.: 12/928,829

(22) Filed: Dec. 20, 2010

(65) Prior Publication Data

US 2011/0098306 A1   Apr. 28, 2011

Related U.S. Application Data

(63) Continuation-in-part of application No. 11/978,335, filed on Oct. 29, 2007, now Pat. No. 7,863,275.

(60) Provisional application No. 60/855,275, filed on Oct. 30, 2006.

(51) Int. Cl.
*A61K 31/4985* (2006.01)

(52) U.S. Cl.
USPC .............. 514/250; 514/249; 544/258; 436/98

(58) Field of Classification Search
USPC .............. 514/249, 250; 544/258; 436/98
See application file for complete search history.

(56) References Cited

U.S. PATENT DOCUMENTS

| 2003/0232835 A1 | 12/2003 | Ishihara et al. ............... 514/251 |
| 2004/0013727 A1 | 1/2004 | Gorissen et al. .............. 424/468 |

OTHER PUBLICATIONS

The Merck Manual, (1999), 17th edition, pp. 221-223.*
Shinozaki, K. et al. Abnormal Biopterin Metabolism is a Major Cause of Impaired Endothelium-Dependent Relaxation Through Nitric Oxide/$O_2$ —Imbalance in Insulin-Resistant Rat Aorta : *Diabetes*, 1999, vol. 48, pp. 2437-2445.
Kawano, N. et al. Identification and Localization of Estrogen Receptor α- and β-positive Cells in Adult Male and Female Mouse intestine at Various Estrogen Levels: *Histochem Cell Biol*, 2004, vol. 121, pp. 399-405.
Knoferl, M. et al. Female Sex Hormoes Regulate Macrophage Function After Trauma-Hemorrhage and Prevent Increased Death Rate From Subsequent Sepsis; *Annals of Surgery*, Jan. 2002, vol. 235, No. 1, pp. 105-112.
Dubuquoy, L. et al. Peroxisome Proliferator-Activated Receptor (PPAR) Gamma: a New Target for the Treatment of Inflammatory Bowel Disease, *Gastroenterol Clin Biol.*, 2000, vol. 24 No. 8-9, pp. 719-724.
Papadakis, K.A. et al. Role of Cytokines in the Pathogenesis of Inflammatory Bowel Disease: *Annual Reviews*, Feb. 2000, vol. 51, pp. 289-298.
Micci, M. et al. Neural Stem Cell Transplantation in the Stomach Rescues Gastric Funcion in Neuronal Nitric Oxide Synthase-Deficient Mice: *Gastroenterology*, 2005, vol. 129, pp. 1817-1824.

* cited by examiner

*Primary Examiner* — Savitha Rao

(57) ABSTRACT

Embodiments of the invention are directed to the treatment of gastroparesis by administering sepiapterin.

3 Claims, 17 Drawing Sheets

TREATMENT FOR GASTROPARESIS USING SEPIAPTERIN

CROSS-REFERENCE TO RELATED APPLICATIONS

This continuation-in-part application claims benefit of priority under 35 U.S.C. 120 of non-provisional application U.S. Ser. No. 11/978,335, filed Oct. 29, 2007, now U.S. Pat. No. 7,863,275, which claims benefit of priority under 35 U.S.C. 119(e) of provisional application U.S. Ser. No. 60/855,275, filed Oct. 30, 2006, now abandoned, the entirety of both of which are hereby incorporated by reference.

FEDERAL FUNDING LEGEND

This invention was made with government support under Grant Numbers R21DKO76704 and 3R1DKO76704-03S1 awarded by the National Institutes of Health. The government has certain rights in the invention.

BACKGROUND OF THE INVENTION

1. Field of the Invention

The present invention relates to the fields of pharmacology and treatment of diseases, particularly gastrointestinal dysfunction. More specifically, the present invention discloses in one aspect the acceleration of gastric emptying by tetrahydrobiopterin (BH4) and derivatives thereof.

2. Description of the Related Art

Gastroparesis is a devastating disease affecting predominantly young women, with a female:male ratio of 4:1 (1). Although a variety of diseases are associated with gastroparesis, the two most common subtypes are diabetes and idiopathic diabetic gastropathy (2-3), a syndrome of delayed gastric emptying leading to nausea, vomiting, postprandiol fullness, abdominal pain and early satiety. Because of its chronic and often intractable nature, the disorder has a tremendous impact on both patients and society (4-5). Long standing and poorly-controlled diabetes results in the disturbance of several gastric functions such as gastric myoelectric activity, antroduodenal motor activity, gastric emptying and gastric visceral sensation (6). Although delayed gastric emptying has long been taken as a hallmark of this condition, in recent reports most experts concur that this correlates poorly if at all with clinical symptoms (6-7). The biggest barrier to the development of effective therapy for gastroparesis has been the lack of understanding of its pathogenesis and/or pathophysiology. Consequently, treatment has been empirical and only partially effective, if at all, in relieving major symptoms.

Normally, gastric motility is regulated in large part by neurons of the enteric nervous system located in the muscle wall (2). These neurons are either excitatory (releasing acetylcholine) or inhibitory (releasing nitric oxide and vasoactive intestinal peptide). Nitric oxide (NO) is the principal non-adrenergic non-cholinergic (NANC) inhibitory neurotransmitter in the gastrointestinal tract and is produced by neuronal NOS, expressed in inhibitory enteric neurons (8-14). NO activates soluble guanylate cyclase (sGC), producing an increase in the intracellular cyclic guanosine-3',5'-monophosphate (cGMP), leading to muscle relaxation (12, 15-17). Nitrergic signaling is particularly responsible for gastric accommodation and pyloric relaxation in response to a meal. The importance of NO in gastric function was established by the findings of pyloric hypertrophy and gastric dilation in mice with a targeted genomic deletion of neuronal nitric oxide synthase (nNOS-/-) (18-19). Vagal modulation of enteric neuronal function (both inhibitory and excitatory) also plays an important role in gastric physiology and is predominantly cholinergic in character (20-21).

Expression of nNOS is distinguished by a remarkable diversity. Different 5' mRNA variants of nNOS are reported in various tissues including the gut (22-26). 5' mRNA variants of nNOS are generated either by alternative promoter usage resulting in different mRNA that encode for the same protein (nNOS alpha, 155 KDa) or alternative splicing encoding NH(2)-terminally truncated proteins (nNOS beta and gamma) that lack the PDZ/GLGF domain for protein-protein interaction (23-24, 26-27). nNOS mutant mice, in which exon 2 (encoding for the PDZ/GLGF motif) and, consequently, full length nNOSalpha, was disrupted, maintain some nNOS expression due to presence of nNOSbeta and nNOSgamma. However, gastric function is severely affected with delayed gastric emptying (18-19). These studies suggest that nNOS-alpha, but not other proteins, are essential for normal gastric motor function. The molecular mechanisms responsible for impaired NO function in diabetes remains incompletely understood with both a decrease (28-29) and an increase (30) in nNOS expression being reported in the literature.

In diabetic gastric dysfunction, antral motility and the co-ordination of pressures between antrum and duodenum are diminished. Antral hypomotility has been recorded with intraluminal transducers in patients with diabetes mellitus. Abnormal gastrointestinal motility in diabetes mellitus is likely multifactorial in origin, reflecting disturbances in enteric and vagal neural activity as well as interstitial cells of Cajal (ICC) and smooth muscle function. Of these, enteric neuropathy may be particularly important (11, 31-35). Several studies of animal models of diabetes have convincingly shown disturbances in enteric nerves, particularly involving nitrergic nerves (36-40). Impairment in nitrergic relaxation resulting from either neuronal loss or dysfunction may contribute to gastropathy in both streptozotoci (STZ) induced diabetes (28, 41) as well as spontaneously diabetic male rats and mice (42). These disturbances provide a rational pathophysiological explanation for observations of decreased gastric compliance and pyloric relaxation noted in diabetic patients. In the absence of effective nitrergic output to muscle, gastric accommodation is impaired, resulting in early satiety and discomfort. Further, a functional obstruction at the gastric outlet due to a non-relaxing pylorus leads to delayed emptying (38, 43-45). Diabetic rats and mice show defects in nitrergic relaxation and nNOS expression before neuronal degeneration in the pyloric sphincter and this was reversed by insulin treatment (28, 38).

Several co-factors are known to be important for nNOS activity, including NADPH, calcium and tetrahydrobiopterin (BH4). Tetrahydrobiopterin regulates the homodimeric conformation of all three isoforms of NOS [endothelial(e)NOS; inducible(i)NOS; neuronal(n)NOS] (46). BH4 also serves as a cofactor for three aromatic amino acid hydroxylases: phenylalanine (PAH), tyrosine hydroxylase (TH), and tryptophan hydroxylase (TPH). Additionally, BH4 is scavenger of oxygen-derived free radicals. BH4 has been clinically investigated as therapy for phenylketonuria (PKC), Parkinson's disease, dystonia, depression, Rett Syndrome, infantile autism, senile dementia, Alzheimer's disease and atherosclerosis. Lack of BH4 biosynthetic genes causes several abnormalities in mice. Incubation with saturating concentrations of tetrahydrobiopterin induces substantial conformational changes in the homodimeric structure of nNOS, yielding a stabilized nNOS dimer with maximal NO-producing activity (47-48). In mice, the highest levels of tetrahydrobiopterin are found in the liver, adrenals and stomach (49). Tetrahydrobiopterin synthesis occurs via two distinct pathways: a de novo synthetic pathway which uses GTP as a precursor and a salvage pathway for preexisting dihydropterins (50-51).

GTP cyclohydrolase 1 (GTPCH1) is the rate-limiting enzyme for tetrahydrobiopterin de novo pathway leading to synthesis of dihydroneopterin triphosphate. Treatment of HEK293 cells with 2,4-diamino-6-hydroxypyrimidine (DAHP), an inhibitor of GTPCH1 leads to depletion of tetrahydrobiopterin, destabilization of the dimeric form of nNOS and enhanced ubiquitinylation of nNOS (52). However, addition of sepiapterin, a precursor of tetrahydrobiopterin in the salvage pathway, completely reverses the effect of DAHP on nNOS destabilization (52-53). In the absence of tetrahydrobiopterin, uncoupling of NO production occurs and electron flow from the reductase domain to the oxygen domain of nNOS is diverted to molecular oxygen rather than L-arginine. This leads to super oxide production; super oxide in turn not only degrades NO, but also forms peroxynitrite a potent oxidant that can rapidly oxidize BH4 to BH3+ and subsequently to BH2. BH2 may compete with tetrahydrobiopterin for nNOS binding, resulting in further impaired nNOS bioactivity.

There is considerable evidence supporting an important role for impairment in the tetrahydrobiopterin biosynthetic pathway in mediating dysfunction of NOS isoforms such as eNOS both in vivo and in vitro. DAHP, a GTPCH1 inhibitor reduces the sensitivity to acetylcholine (endothelium-dependent)-induced vascular relaxation (mediated by NO) in normal mice and this inhibitory effect was shown to be restored by addition of tetrahydrobiopterin in vitro (54). Treatment of diabetic vascular endothelial cells with sepiapterin (the tetrahydrobiopterin precursor in the salvage pathway, (FIG. 1), significantly improves NO synthesis. Preincubation of vascular rings with either tetrahydrobiopterin or sepiapterin enhances Ach (acetylcholine-)-induced relaxation in diabetic mice (55-57). In addition, dietary supplementation of sepiapterin increases ACh-induced vascular relaxation in diabetic mice (54). In cultured endothelial cells exposed to high glucose (58), ex vivo gene transfer of GTPCH1 restores eNOS dimerization, attenuates impaired endothelium-dependent relaxation and increases NO production (59-60). Selectively augmenting endogenous tetrahydrobiopterin levels by targeting over expression of GTPCH in endothelial cells in vivo preserves eNOS dimerization in streptozotocin (STZ)-induced diabetes mice (59, 61). The beneficial effects of tetrahydrobiopterin supplementation in reversing impaired endothelium dependent relaxation have also been demonstrated in human patients. BH4 therapy was shown to be useful in improving endothelium-dependent relaxation in patients with hypercholesteromia (62), venous conduits used for coronary artery bypass graft surgery (63), patients with type II diabetes (64), normal epicardial arteries and smokers (65).

Furthermore, there is increasing evidence of gender-related differences in gastric emptying. The effect of gender in a healthy population on gastric emptying remains controversial though it appears that women may have slower solid and liquid emptying. Ambulatory antroduodenal manometry has shown shorter migrating motor complex (MMC) periods in women compared to men (66). The mechanisms responsible for these differences are not completely understood. In a recent study of duodenojejunal motility, women in the follicular phase were found to exhibit motor activity similar to that of men (67). On the other hand, another study demonstrated attenuated postprandial antral contractile activity in the follicular phase of women compared to men (68). Additionally, animal studies demonstrated that the gastric emptying rate was slower in ovary-intact female rats compared to ovariectomized (depletion of ovarian hormones; estrogen and progesterone) female rats (69-70). Furthermore, studies suggested that estradiol-17β (E2) but not progesterone (P4) may be responsible for delayed gastric emptying and increased nitrergic system. In addition to this, studies suggest that P4 treatment decreased the resting tension fundus, inhibited mean contractile amplitude of antrum and the motility index of pylorus in rats (71). Diabetes induction decreases both the circulatory E2 and P4 levels in both women and female rats (72-76).

Sex steroid hormones mediate their biological actions through their respective nuclear (genomic) cytoplasmic/membrane (non-genomic, rapid via nitric oxide elevation) receptors (77). Estrogen receptors (ERs) and progesterone receptors (PRs) are expressed as two proteins: ERα and ERβ, and PR-A and PR-B. ERα and ERβ are expressed from two different genes, whereas PR isoforms are produced from alternate use of two promoters from the same gene. Sex steroid hormone receptors require both a ligand (sex hormones, insulin, growth factors etc) and interactions with other proteins, such as coregulators, to achieve maximal transcriptional activation of genes. Female sex steroids (both $E_2$ and $P_4$) has multiple beneficial actions that includes neuroprotection, maintaining glucose homeostasis in both health and diabetes (74, 76-78). In particular, estrogen has both genomic and rapid nongenomic effects via its receptors on vascular endothelium, including activation of NO synthesis (79-80). Previous studies demonstrated that nNOS is involved in estrogen mediated neuroprotection in neuroblastoma cells (81-86). The role of progesterone and its metabolites via PR's on NO mediated cardioprotection has been recently reported in postmenopausal women (87).

Upon binding to their respective receptors, sex steroids, utilizes several cell signaling mechanisms such as cyclic adenosine monophosphate (cAMP), cyclic guanosine monophosphate (cGMP), mitogen-activated protein kinases (MAPKs), phosphatidylinositol 3-kinase (PI3K)/Akt pathways, for their actions. In the genomic pathway, sex steroids binds to their cytosolic/nuclear receptors, leading to activation of MAPK/Akt, increase gene transcription and upregulate nitric oxide production. In non-genomic pathway, sex steroids binds to their membrane receptors, which are coupled to increased $Ca^{2+}$ release from the endoplasmic reticulum, and stimulate MAPK/Akt/PI3K pathway, leading to NO production. NO diffuses into the smooth muscle cells, binds to adenylate cyclase (AC) or guanylate cyclase (GC) and increases cAMP or cGMP respectively. Significant actions for sex steroids have been noticed in the gastrointestinal tract in various experimental animal models and human clinical settings (88). Shah et al studies demonstrated that estrogen treatment increases nNOS positive neurons in the female rat stomach. Several studies demonstrated that both ERs are primarily localized in nerve cells of the gut (88-89).

Estrogen treatment elevates both the expression of GTPCH1 and BH4 levels in rat brain neurons through estrogen receptors (90-92). In vitro hyperglycemia decreases both BH4 biosynthesis and nitric oxide and estrogen supplementation restored this effect via ERα in bovine aortic endothelial cell culture (93). Diabetes induction decreases the circulatory estrogen and progesterone levels in both women and female rats. Previous reports demonstrated that estrogen receptors are localized in stomach enteric neurons. The beneficial role for $E_2$ treatment on both GTP cyclohydrolase1 (GTPCH1) expression and nNOS expression has been well demonstrated.

Despite this, the prior art is deficient in the role played by tetrahydrobiopterin or derivatives thereof in the nitric oxide induced diabetic gastroparesis. Additionally, the prior art is also deficient in understanding the gender-related differences in gastric emptying. The present invention fulfills this long-standing need and desire in the art.

SUMMARY OF THE INVENTION

In one embodiment of the present invention, there is provided a method of restoring gut motility in an individual. This method comprises administering a pharmacologically effective amount of sepiapterin, tetrahydrobiopterin, sex steroid hormone or a derivative thereof or a compound(s) that increases the expression and/or activity of enzymes molecules that are critical in the synthesis of tetrahydrobiopterin or compounds that stimulate steroid receptor to the individual, thereby restoring gut motility in the individual.

In another embodiment of the present invention, there is a method of determining the risk of developing gastrointestinal dysfunction in an individual. Such a method comprises obtaining a biological sample from the individual, determining the level of tetrahydrobiopterin, activity level of enzymes or molecules that are critical in the synthesis of tetrahydrobiopterin, activity level of sex steroid hormones, sex steroid hormone receptor level or a combination thereof in the individual. The level of tetrahydrobiopterin activity level of the enzymes or the molecules, the level of sex steroid hormone activity, the sex steroid hormone receptor level or a combination thereof in this sample are then compared with the level of tetrahydrobiopterin activity level of the enzymes or the molecules, the level of sex steroid hormone activity, the sex steroid hormone receptor level or a combination thereof in the sample of control individual, where a reduced level of tetrahydrobiopterin, activity level of the enzymes or the molecules, the level of sex steroid hormone activity, the sex steroid hormone receptor level or a combination thereof compared to the level in the sample of control individual indicates that the individual has more risk of developing gastrointestinal dysfunction.

In yet another embodiment of the present invention, there is a method of determining risk of developing gastrointestinal dysfunction in an individual. This method comprises detecting variations in one or more genes encoding one or more enzymes that are critical in the synthesis of tetrahydrobiopterin, encoding one or more receptors of sex steroid hormones, mutations in BH4 biosynthesis genes or mutations in one or more genes encoding hormones associated with diabetes or a combination thereof in a sample of the individual, where presence of at least one of variations or mutations in one or more genes in the sample of the individual compared to one or more genes in the control sample indicates that the individual is at risk of developing gastrointestinal dysfunction.

BRIEF DESCRIPTION OF THE DRAWINGS

FIG. 2A shows gender and diabetes induced changes in solid gastric emptying in rats. The rate of gastric emptying was measured during the 4 hours experimental time. FIG. 2B shows that dietary supplementation (25 mg/kg b.w./day/rat), completely restored gastric emptying in female rats. *p<0.05. ANOVA.

FIG. 4A shows effect of diabetes on gastric nitrergic relaxation in response to transmural nerve stimulation (2 Hz) in age-matched male and female rats. Active tone was induced initially with 30 µM 5-hydroxytryptamine. The nitric oxide (NO) dependence relaxation in female control (FC) and female diabetic (FD) groups was confirmed by preincubation with the NO inhibitor, L-NAME (LNM, $10^{-4}$M). Each point represents mean±SEM from 4-6 animals in each group. *significant inhibition with L-NAME, #*significant inhibition with L-NAME, $p<0.05 for FD vs FC. ANOVA. AUC. FIG. 4B shows effect of nitric oxide donor, DETA-NONOate on gastric relaxation. Gastric pyloric tissue segments from normal and diabetic female rats were preincubated with DETA-NONOate for 10-15 minutes and changes in relaxation were analysed. FIG. 4C shows tunnel staining (counterstaining with hematoxylin) in female rat gastric pylorus myenteric neurons. No staining for TUNNEL was noticed in diabetic gastric tissues compared to controls indicating that there were no neuronal cell death. Arrows indicate a portion of myenteric plexus region. Magnifications are 200×.

FIGS. 5F-5G show nNOS dimer (310 KDa, top band) and monomer (155 KDa, bottom band) ration in gastric tissue of female control (FC) and female diabetes (FD). Densitometric analysis followed by ratio of nNOS alpha dimerization to beta-tubulin were calculated. The bars represent mean±SEM, n=3-4, *p<0.05 control vs diabetic, ANOVA.

FIG. 12A shows effect of exogenous BH4 (100 μM, 30 minutes) on nitrergic relaxation in female control (FC) and diabetic (FD) rats. Basal tone relaxation studies in gastric tissues were performed after EFS stimulation (n=2). Exogenous BH4 increased nitrergic relaxation in female diabetic gastric fundal tissues. AUC=area under curve. FIG. 12B shows that chronic diabetes delayed gastric emptying for solids in female rats. In vivo dietary BH4 supplementation (25 mg/Kg body weight/day/rat/3 Wk), completely restored delayed gastric emptying in female rats. (n=4-6). *p<0.05. FIG. 12C shows effect of dietary BH4 on gastric nNOS activity in female diabetic rats. Diabetic induction reduced nNOS activity in gastric tissues. Dietary BH4 supplementation partially restored altered gastric emptying in female diabetics (n=2).

FIG. 13A shows effect of dietary BH4 on intragastric pressure (IGP, mmHg× sec) and FIGS. 13B-13C show gastric nNOS alpha protein expression in female diabetic rats. Diabetic induction elevated IGP and reduced nNOSalpha expression in gastric tissues. Dietary BH4 supplementation completely restored altered IGP and nNOS alpha protein expression (n=4).

FIG. 20A shows (MTX)-induced nitrergic relaxation in female diabetic rats in vivo. Nitrergic relaxation was measured following daily exposure to intraperitoneal injection (i.p) of MTX (3.75 mg kg$^{-1}$ body wt, two times a day), for 4 days. The values are mean±SE of 4-6 animals. Statistical significance was determined by student t-test. *p<0.05 compared with control group. FIGS. 20B-20C shows the effect of MTX-induced nNOSalpha dimer expression in female diabetic rats in vivo. Western blot (FIG. 20B) was done following daily exposure to MTX (3.75 mg kg$^{-1}$ body wt, two times a day), for 4 days. Representative immunoblot and densitometric analysis data for nNOSalpha protein dimerization in female rat gastric antrum. Values are mean±SE (N=4). Statistical significance was determined by Tukey test after one-way ANOVA. *p<0.05 compared with control group; #p< compared with MTX group. FIG. 20D shows the effect of MTX and SEP supplementation on NO release in female diabetic rats in vitro. NO levels are measured using the NO assay kit following 48 h incubation with MTX (100 μM), MTX+SEP (100 μM, 100 μM). Values are mean±SE (N=4-6). Statistical significance was determined by Tukey test after one-way ANOVA. *p<0.05 compared with control group; #p< compared with MTX group.

FIGS. 21A-21B: Representative immunoblot and densitometric analysis data for nNOSalpha protein expression in female control rat gastric antrum supplemented with either BH$_4$ or SEP. FIGS. 21C-21D: Representative immunoblot and densitometric analysis data for nNOSalpha protein expression in female diabetic rat gastric antrum. FIGS. 21E-21F: Representative immunoblot and densitometric analysis data for nNOSalpha protein dimerization in female control rat gastric antrum supplemented with either BH$_4$ or SEP. FIGS. 21G-21H: Representative immunoblot and densitometric analysis data for nNOSalpha protein dimerization in female diabetic rat gastric antrum. Values are mean±SE (n=4). Statistical significance was determined by Tukey test after one-way ANOVA. *p<0.05 compared with control group; #p< compared with DB group.

DETAILED DESCRIPTION OF THE INVENTION

Figure 1:
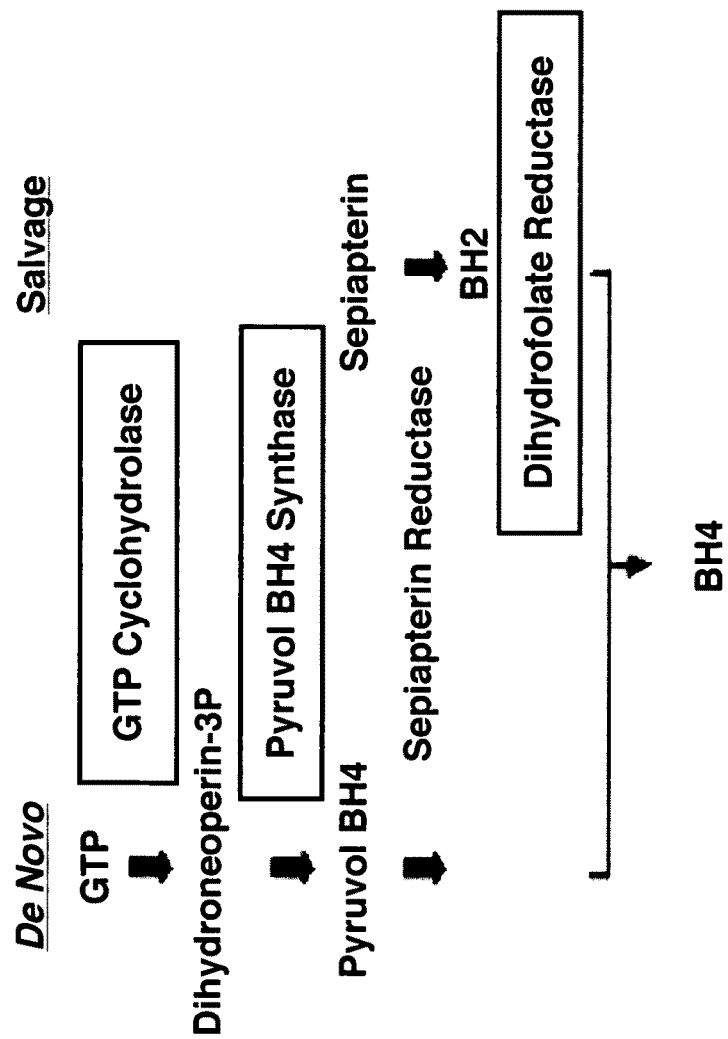
FIG. 1 shows biosynthesis of tetrahydrobiopterin (BH4). BH2=dihydrobiopterin, GTP=guanosinetriphosphate.

As used herein, the term, "a" or "an" may mean one or more. As used herein in the claim(s), when used in conjunction with the word "comprising", the words "a" or "an" may mean one or more than one. As used herein, the term "or" in the claims refers to "and/or" unless explicitly indicated to refer to alternatives only or the alternatives are mutually exclusive, although the disclosure supports a definition that refers to only alternatives and "and/or".

As used herein "another" or "other" may mean at least a second or more of the same or different claim element or components thereof.

As used herein, the term "contacting" refers to any suitable method of bringing the composition described herein into contact with a cell of gastric tissue. In vitro or ex vivo this is achieved by exposing the cell to the composition in a suitable medium. For in vivo applications, any known method of administration is suitable as described herein.

As used herein, the term "compound" or "agonist" or "antagonist" means a molecular entity of natural, semi-synthetic or synthetic origin that either activates or blocks, stops, inhibits, and/or suppresses biosynthetic pathway of tetrahydrobiopterin. An agonist will activate the pathway while the antagonist will block, inhibit, and/or suppress the pathway As used herein, "sepiapterin, tetrahydrobiopterin or derivative thereof" may be of a natural, semi-synthetic or synthetic origin that restore dimerization of neuronal nitric oxide synthase and activity of neuronal nitric oxide synthase, lower TNF alpha level, NF-kB, free radicals, restore nitric oxide level and restore nitrergic relaxation of gut tissue. These compounds may be administered independently, either systemically or locally, by any method standard in the art. Dosage formulations of these compounds may comprise conventional non-toxic, physiologically or pharmaceutically acceptable carriers or vehicles suitable for the method of administration and are well known to an individual having ordinary skill in this art.

Abnormalities in gastric motility occur in 20-55% and up to 30% of patients with Type I (insulin-dependent) and Type II diabetes (non-insulin-dependent), respectively. Symptoms of diabetic gastropathy ranges from mild dyspepsia to recurrent vomiting and abdominal pain. Despite the high frequency of occurrence of diabetic gastric dysfunction, its pathogenesis remains poorly understood. Additionally although up to 80% of the patients with diabetic gastroparesis are women, the mechanisms responsible for these gender differences remain completely unknown.

Nitric oxide (NO), synthesized by neuronal nitric oxide synthase (nNOS) in the myenteric neurons is a major regulator of gastrointestinal motility in health. Several lines of experimental work also indicate a potentially important role for nitrergic dysfunction in the pathogenesis of diabetic gastroparesis. The present invention investigated whether gender differences in nitrergic control of gastric motility accounted for observed vulnerability of females to diabetic gastroparesis. Briefly, diabetes was induced by streptozotocin (STZ; 55 mg per kg body weight, i.p.) and experiments were conducted 12 weeks after diabetes induction. The nNOS protein expression and dimerization were examined using COOH- and NH2-terminal antibodies, respectively. The COOH-terminal antibody detects all forms of nNOS whereas the NH2-terminal antibody detects only wild type (full length) nNOS alpha proteins. Under normal conditions, both dimers and monomers of nNOS protein were intensified at 155 KDa. However, low temperature (LT) SDS-PAGE separate NOS dimers (310 KDa) and monomers (155 KDa) from non-boiled sample homogenates.

In summary, the present invention discloses that significant gender differences in gastric nitrergic function exists in both healthy and diseased individuals. These differences are not accounted for by changes in the neuronal loss or nNOS expression but correlate with changes in nNOS dimerization. Females with diabetes show a selective reduction in nitrergic relaxation of the pylorus, accompanied by impairment in nNOS dimerization, nNOS activity, NO release and decreased tetrahydrobiopterin and GTPCH1 levels. Additionally, diabetes induction decreases estrogen receptor (ER) alpha expression in female gastric tissues. Further, in vivo experiments demonstrate that dietary BH4 delayed gastric emptying, intragastric pressure (IGP) and nNOS activity in female diabetics. Additionally, it was observed that diabetic females exhibited decreased body weights. Pup weights have been reported to have drastically reduced in PTPS ($2^{nd}$ enzyme in de novo BH4 synthesis pathway) knockout mice. Studies have also demonstrated that IGF1 levels are reduced up to 7 fold in BH4 deficient patients. In the present invention, it was observed that BH4 supplementation restored the body weights in female diabetic rats. Taken together, this suggests that BH4 may have a beneficial role in improving total body weights and survival perhaps by involving IGF1.

Furthermore, in vitro experiments suggest that endogenous tetrahydrobiopterin inhibition reduced gastric nNOS dimerization, NO release and nitrergic relaxation. Therefore, BH4 supplementation may restore nitrergic relaxation in diabetic gastric tissue. Reactive Oxygen species (ROS) staining was higher in female diabetic gastric cross sections. BH4 treatment reduced the intensity of staining in diabetic females. These data demonstrated that BH4 acts as antioxidant as well as anti-inflammatory agent in other disease states, Additionally, serum sex hormones and the expression of gastric ER-alpha was decreased after diabetic induction in female rats. In vivo estradiol-17beta ($E_2$) treatment delayed solid gastric emptying in healthy females due to elevated levels of nNOS alpha. Conversely, $E_2$ treatment normalized delayed gastric emptying and decreased nNOSalpha protein expression in female diabetic rats. Additionally, tetrahydrobiopterin decreased elevated TNF-alpha levels in female diabetic rat circulation. Elevated TNF alpha might have harmful effects such as increasing oxidative stress factors and apoptosis (including neuropathy) in multiple tissues, altering nitric oxide levels and causing gastroparesis in diabetic patients.

Thus, the present invention discloses a method of regulating levels of agonists and antagonists of gut motility by contacting a cell in gastric tissue with a pharmacologically effective amount of sepiapterin, tetrahydrobiopterin, sex steroid hormone or a derivative thereof or a compound(s) that increases the expression and/or activity of enzymes or molecules that are critical in the synthesis of tetrahydrobiopterin to the individual, thereby regulating the levels of agonists and antagonists of gut motility. Examples of the agonists of gut motility may include but are not limited to neuronal nitric oxide synthase or monoamine neurotransmitters and those of antagonists of gut motility may include but are not limited to free radicals, NE-κB or inflammatory cytokines.

Overall, the findings discussed herein indicate that diabetes negatively affects both female sex steroid hormones and gastric tetrahydrobiopterin biosynthesis. This results in decreased nNOS activity and NO production, thereby impairing nitrergic relaxation. Thus, supplementation of the diet of individuals diagnosed with, suspected of or likely to suffer from diabetes with tetrahydrobiopterin or derivatives thereof or with compound(s) that increase the expression and/or activity of enzymes or molecules that are critical in the synthesis of tetrahydrobiopterin and/or sex steroid hormones or derivatives thereof might restore impaired nNOS activity and function. The present invention contemplates that use of sepiapterin, tetrahydrobiopterin or derivatives thereof and sex steroid hormones or derivatives thereof is significant since the methods discussed herein can be used to treat gastroparesis. Specifically, the gastroparesis may be caused due to diabetes, adrenal or thyroid gland dysfunctions, scars or fibrous tissue from ulcers or tumors, drugs that weaken the stomach, previous stomach surgery, anorexia, bulimia, neurologic or brain disorders, lupus erythematosus or scleroderma.

Furthermore, the administration of sepiapterin, tetrahydrobiopterin, sex steroid hormones or a derivative thereof or compound(s) that increase the expression and/or activity of enzymes or molecules that are critical in the synthesis of tetrahydrobiopterin is also useful in restoring gut motility in individuals with esophagus and/or small or large intestinal bowel disorders caused by impaired nitric oxide synthase and/or monoamine neurotransmitter function and/or gut related diseases. Examples of such gut related disease include but are not limited to pancreatitis, colon cancer, colonic inflammation, Crohn's disease, inflammatory bowel disease or irritable bowel syndrome. Furthermore, the levels of BH4 and/or levels of enzymes such as GTP cyclohydrolase I or other molecules critical in BH4 synthesis may be used as a diagnostic marker to predict the risk of developing gastroparesis. Additionally, it is also contemplated that the variations in the genes encoding BH4, the enzymes (GTP cyclohydrolase 1) or other molecules critical in BH4 synthesis may be helpful in predicting predisposition to developing gastroparesis. Hence, this could be a clinically useful diagnostic test.

The present invention is directed to a method of restoring gut motility in an individual, comprising administering a pharmacologically effective amount of sepiapterin, tetrahydrobiopterin, sex steroid hormone or a derivative thereof or a compound(s) that increases the expression and/or activity of enzymes, molecules that are critical in the synthesis of tetrahydrobiopterin or compounds that stimulate steroid receptor to the individual, thereby restoring gut motility in the individual. This method may further treat or prevent a gut-related disorder in the individual. The causes of the prevention or treatment of the disorder are not limited to but may include restoration of intragastric pressure, restoration of body weight, improvement in gastric emptying, in symptoms of gastroparesis, in mast cell diversity and function, in blood flow, prevention of free radical induced-damage or free radical-induced apoptosis of neurons or other cellular components or a combination thereof in the individual. The gut-related disorder may include but is not limited to gastroparesis, esophagus and/or small and large intestinal bowel disorders caused by impaired nitric oxide synthase and/or monoamine neurotransmitter function, pancreatitis, colon cancer, colonic inflammation, Crohn's disease, inflammatory bowel disease or irritable bowel syndrome. The cause of gastroparesis in such individuals may include but is not limited to diabetes, adrenal or thyroid gland dysfunction, scars or fibrous tissue, drugs that weaken the stomach, previous stomach surgery, anorexia, bulimia, neurologic or brain disorders, lupus erythematosus or scleroderma. Additionally, examples of the drugs that weaken the stomach may include but are not limited to tricyclic antidepressants, calcium blockers or drugs used to treat irritable bowel syndrome.

The administration of compounds discussed supra may restore body weight, restore dimerization of the neuronal nitric oxide synthase, restore activity of the neuronal nitric oxide synthase, restore functions of monoamine neurotransmitters, lower the level of free radicals, suppress stimulation of NF-κB, suppresses inflammatory signaling, lower the level(s) of inflammatory cytokine(s) or a combination thereof. Examples of the monoamine neurotransmitters may include but are not limited to dopamine, epinephrine, norepinephrine, serotonin or melatonin and that of the inflammatory cytokine may include but is not limited to TNF-alpha.

Additionally, the sepiapterin, the tetrahydrobiopterin or the derivative thereof or a compound(s) that increases the expression and activity of enzyme(s) or molecule(s) that are critical in the synthesis of tetrahydrobiopterin may be administered either alone or in combination with other medications. Example of the enzyme inhibited may include but is not limited to GTP cyclohydrolase 1. Further, example of the derivative of sepiapterin may include but is not limited to 7,8-dihydrobiopterin, the derivative of tetrahydrobiopterin may include but is not limited to 6R-tetrahydrobiopterin, lipoic acid, dihydrolipoic acid, a salt thereof or a combination thereof and the sex steroid hormone may include but is not limited to estradiol-17beta, phytoestrogens, isoflavones or progesterone. The compounds that stimulate sex steroid hormone receptors such as estrogen receptor or progesterone receptor may include but is not limited to agonists for steroid hormone receptors, growth hormones or insulin.

The present invention is also directed to a method of determining the risk of developing gastrointestinal dysfunction in an individual, comprising obtaining a biological sample from the individual, determining the level of tetrahydrobiopterin, activity level of enzymes or molecules critical in the synthesis of tetrahydrobiopterin, activity level of sex steroid hormones, sex steroid hormone receptor level or a combination thereof; and comparing the level of tetrahydrobiopterin, activity level of the enzymes or the molecules, activity level of sex steroid hormones, sex steroid hormone receptor level or a combination thereof in the sample of the individual with the level of tetrahydrobiopterin activity, level of the enzymes or the molecules, activity level of sex steroid hormones, sex steroid hormone receptor level or a combination thereof in the sample of a control individual where a reduced level of tetrahydrobiopterin, activity level of the enzyme or the molecules, activity level of sex steroid hormones, sex steroid hormone receptor level or a combination thereof compared to the level in the sample of the control individual indicates that the individual has more risk of developing gastrointestinal dysfunction. Generally, the individual who may benefit from such a method may include but is not limited to one with impaired nitric oxide synthase and/or monoamine neurotransmitter function, diabetes, elevated levels of NF-κB and/or inflammatory cytokines, adrenal or thyroid gland dysfunctions, scars or fibrous tissue, previous stomach surgery, anorexia, bulimia, neurologic or brain disorders, lupus erythematosus, scleroderma, or who is taking drugs that weaken the stomach. Examples of the gastrointestinal dysfunction may include but is not limited to gastroparesis, inflammatory bowel disease, esophagus or small and large intestinal bowel disorders, pancreatitis, colon cancer, colonic inflammation, Crohn's disease or irritable bowel syndrome. Example of the biological sample may include, but is not limited, to serum, gut, vasculature or reproductive organs. All other aspects regarding the example of inflammatory cytokine, drugs that weaken the stomach, and the enzyme whose activity or level is determined is the same as discussed supra.

The present invention is also directed to a method of determining risk of developing gastrointestinal dysfunction in an individual, comprising: detecting variations in one or more genes encoding one or more enzymes that are critical in the synthesis of tetrahydrobiopterin, encoding one or more receptors of sex steroid hormones, mutations in BH4 biosynthesis genes or mutations in one or more genes encoding hormones associated with diabetes or a combination thereof in a sample of the individual, where presence of at least one of variations or mutations in one or more genes in the sample of the individual compared to one or more genes in the control sample indicates that the individual is at risk of developing gastrointestinal dysfunction. All other aspects regarding the individual benefiting from such a method, the type of inflammatory cytokine, the examples of drugs that weaken the stomach, the examples of gastrointestinal dysfunction, the example of enzyme whose gene variation is assessed and the examples of samples used to determine the variations is same as discussed supra. The genes encoding hormones associated with diabetes are known in the art. These include but are not limited to insulin or glucagon.

The compounds described herein may be administered independently or in combination with another drug or compound that is routinely used to treat other symptoms of that specific disorder and may comprise one or more administrations to achieve, maintain or improve upon a therapeutic effect. It is well within the skill of an artisan to determine dosage or whether a suitable dosage of the composition comprises a single administered dose or multiple administered doses. An appropriate dosage depends on the subject's health, the restoration of mucosal barrier function or attenuation of inflammation, the route of administration and the formulation used. Examples of such drugs may include but are not limited to tricyclic antidepressants, calcium blockers or drugs used to treat irritable bowel syndrome.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Methods and Materials
Experimental Rats and Induction of Diabetes

Adult female Sprague Dawley rats (9 week old) were procured from Harlan (Houston, Tex.) and Harlan Sprague Dawley Inc. (Indianapolis, Ind.) and maintained in the institutional animal care facility under controlled temperature, humidity and light-dark cycle (12:12-h), with free access to rodent chow and water. All experiments in this study were approved by the Institutional Animal Care and Use Committees at the University of Texas Medical Branch, Galveston, Tex. and Meharry Medical College, Nashville, Tenn., in accordance with the recommendations of National Institutes of Health, Guide for the Care and Use of Laboratory Animals.

Diabetes was induced in overnight fasted animals by a single intraperitoneal injection of streptozotocin (STZ, 55 mg $kg^{-1}$) (Sigma Chemical, St. Louis, Mo.) prepared in 9 mmol citrate buffer, pH 4.0. Control animals were injected with the vehicle (9 mmol citrate buffer, pH 4.0) (94). Blood glucose levels were examined in overnight fasted animals, 48 h post STZ injection. Animals exhibiting blood glucose levels more than 250 mg $dl^{-1}$ were considered diabetic and included in the study. Blood glucose levels in vehicle-treated overnight fasting rats ranged between 80-95 mg $dl^{-1}$. Both control and diabetic female rats were selected during the diestrous phase of the estrous cycle using vaginal smear testing method [by measuring vaginal cytology (90-100% of leucocytes) under microscope] for further experiments. As reported earlier, 60-70% of diabetic rats show a persistent diestrous stage of the estrous cycle (data not shown) (95-96).

Experimental Design

At the end of $7^{th}$ week of diabetes induction, animals were divided into four groups, i.e. control female rats (C), diabetic female rats (DB), $BH_4$ supplemented diabetic female rats (DB+$BH_4$) and SEP supplemented diabetic female rats (DB+SEP). DB+$BH_4$ were provided with $BH_4$ pellets (20 mg $kg^{-1}$ body wt $day^{-1}$) for next 2 weeks. DB+SEP were provided with SEP tablets (20 mg $kg^{-1}$ body wt $day^{-1}$ for 10 days. $BH_4$ or SEP pellets (one gram size flavored with chocolate, TestDiet, Land O'Lakes Purina Feed, LLC, Richmond, Ind.) were fed to each animal housed in a separate cage before they were fed with normal rat chow. A 20 mg $kg^{-1}$ $BH_4$/SEP dose was selected based on the published studies (97-98). In addition, in our recent report two doses for $BH_4$ (5 and 20 mg $kg^{-1}$) were used for gastric motility studies and no significant difference between the two doses was found (99). Therefore a 20 mg $kg^{-1}$ dose for $BH_4$/SEP was chosen. On the last day of $BH_4$ and SEP supplementation, animals were sacrificed to collect gastric muscular tissue for future analysis. Tissue samples were snap frozen in liquid nitrogen and stored at −80° C. until analyzed. $BH_4$ or SEP-pellets used in this study were prepared by compressing (Schircks Laboratories, Switzerland) with rodent chow and stored at −20° C. until used. To avoid oxidation of $BH_4$ or SEP, heat and water was not employed in pellet preparation.

Solid Gastric Emptying Studies

At the end of 10 days of SEP supplementation solid gastric emptying studies were performed according to the method of Martinez et al. with slight modification (94, 100) Our recent published data using this protocol demonstrate that there are gender differences exist in solid gastric emptying and $BH_4$ treatment restores delayed gastric emptying only in female but not in males in the onset of diabetes (94, 99). In addition, using the similar gastric emptying protocol, accelerated gastric emptying was observed instead of delayed gastric emptying in spontaneous diabetic female but not in male diabetic animals (101). It was observed that 60-70% diabetic rats displayed delayed gastric emptying as reported in humans in the onset of diabetes.

According to the protocol, animals were fasted over night (provide water). On the next day, known amount of food was fed to the animals for 3 h. At the end of 3 h collected the remaining food from the cage and calculated the amount of food intake. Then fast the animals for 4 hrs without food and water. At the end of fast, animals were euthanized, collected the gastric tissue and measured the weight of the whole stomach. Then removed the food contents by opening the stomach and measured the empty stomach weight. The rate of gastric emptying was calculated according to the following equation: gastric emptying (% in 4 h)=(1−gastric content food intake$^-$$_1$)×100.

Organ Bath Studies

Electric field stimulation (EFS)-induced NANC relaxation was studied in circular gastric antrum muscle strips. Muscle strips were tied with silk thread at both ends and were mounted in 10-ml water-jacketed organ baths containing Krebs buffer (11 mM glucose) at 37° C. and continuously bubbled with 95% $O_2$-5% $CO_2$ (Radnoti Glass Technology, Monrovia, Calif.). Tension for each muscle strip was monitored with an isometric force transducer and analyzed by a digital recording system (Biopac Systems, Santa Barbara, Calif.). A passive tension equal to 2 g was applied on each strip in the 1 h equilibration period through an incremental increase (0.5 g, four times, at 15 min interval). Gastric antrum muscle strips were exposed to atropine, phentolamine and propranolol (10 µmol each) in bath solution for 1 h to block cholinergic and adrenergic responses. 5-hydroxytryptamine (5-HT; 100 µM) pre-contracted strips were exposed to EFS (90 V, 2 Hz, 1-ms pulse for duration of 1 min) to elicit NANC relaxation. Relaxation response elicited by low frequency (EFS; 2 Hz) stimulus under NANC conditions, as used in this study, was demonstrated as predominantly nitrergic in origin (94, 101).

To investigate the in vivo effect of methotrexate (MTX) on EFS induced nitrergic relaxation; a group of animals were supplemented with MTX (inhibitor of dihydro folate reductase, DHFR) 3.75 mg kg$^{-1}$ body wt. per twice a day for 4 days. Gastric strips from control animals and MTX treated animals were incubated in organ bath and nitrergic relaxation was measured by EFS. At the end of each experiment, the muscle strip was blotted dry with filter paper and weighed. Comparisons between groups were performed by measuring the area under the curve (AUC mg$^{-1}$ tissue) of the EFS-induced relaxation ($AUC_R$) for 1 min and the baseline for 1 min ($AUC_B$) according to the formula ($AUC_R$-$AUC_B$) weight of tissue (mg)$^{-1}$=AUC mg of tissue$^{-1}$.

In Vitro NO Release

Animals from control groups were killed by $CO_2$ asphyxiation, the abdominal cavity opened, and the stomach dissected and transferred in chilled oxygenated Krebs bicarbonate solution of the following composition (in mmol): 118.0 NaCl, 4.7 KCl, 25.0 $NaHCO_3$, 1.5 $CaCl_2$, 1.2 $MgSO_4$, 1.2 $KH_2PO_4$, and 11.5 glucose (pH 7.4). Antrum tissue was harvested and cut into mucosa-free strips and were cultured for 48 h (37° C., 5% $CO_2$) in 500 ml of phenol red-free DMEM supplemented with NB27 (2%) and antibiotics (1%) in the presence of normal glucose (control), control+MTX (100 µM), control+MTX+SEP (100 µM, 100 µM). On completion of incubation, DMEM (500 ml) was collected and stored at −80° C. for analysis of NO released in medium during incubation period. NO released in the medium was analyzed as total nitrite (metabolic byproduct of NO) following the protocol supplied with a commercially available kit (EMD Chemicals, Gibbstown, N.J.).

Western Blot Analysis nNOSa protein was quantified in gastric antrum homogenates from all groups using standard western blot analysis, as described in our previous study (94). Proteins were measured by Bio-Rad protein assay (Bio-Rad, Hercules, Calif.) and 30 µg protein was separated by 6% SDS polyacrylamide gel electrophoresis (SDS-PAGE). The membrane was immunoblotted with polyclonal nNOSa primary antibody (Zymed Laboratories Inc., CA) and anti-rabbit IgG conjugated with horseradish peroxidase (Sigma Chemical, St. Louis, Mo.) as secondary antibody. Binding of antibodies to the blots was detected with enhanced chemiluminescence system (ECL, Amersham Pharmacia Biotech, Piscataway, N.J.) following manufacturer's instructions. Stripped blots were re-probed with g-tubulin specific polyclonal antibodies (Sigma Chemical, St. Louis, Mo.) to enable normalization of signals between samples. Band intensities were analyzed using Bio-Rad Gel Doc (Bio-Rad, Hercules, Calif.).

nNOSalpha Dimerization in Rat Gastric Antrum

Levels of nNOSa monomer and dimer were quantified by western blotting via Low temperature (LT)-PAGE in gastric antrum homogenates as described previously (94). LT-SDS-PAGE was performed on ice. The low-temperature process was used to identify nNOS dimers and monomers in the native state as low temperature is known to prevent monomerization of nNOS dimmers. For the low-temperature processing, 30 µg of protein in standard Laemmli buffer at 4° C. was used for SDS-PAGE. The mixture was incubated at 0° C. for 30 min before LT-SDS-PAGE using a 6% separating gel. All gels and buffers were pre-equilibrated to 4° C. prior to electrophoresis and the buffer tank placed in an ice-bath during electrophoresis to maintain the gel temperature below 15° C. A polyclonal antibody specific to nNOSa (Zymed Laboratories) and anti-rabbit IgG conjugated with horseradish peroxidase (Sigma Chemical, St. Louis, Mo.) were used as the primary and secondary antibodies, respectively.

Statistics

Data were presented as mean±standard error (SE). Statistical comparisons between groups were determined by Student's t-test or the Tukey test after one-way analysis of variance (ANOVA), using GraphPad prism Version 5.0 (GraphPad software, San Diego, Calif.). A p value of less than 0.05 was considered statistically significant.

EXAMPLE 2

Chronic Diabetes Delayed Solid Gastric Emptying in Rats

Figure 2A:
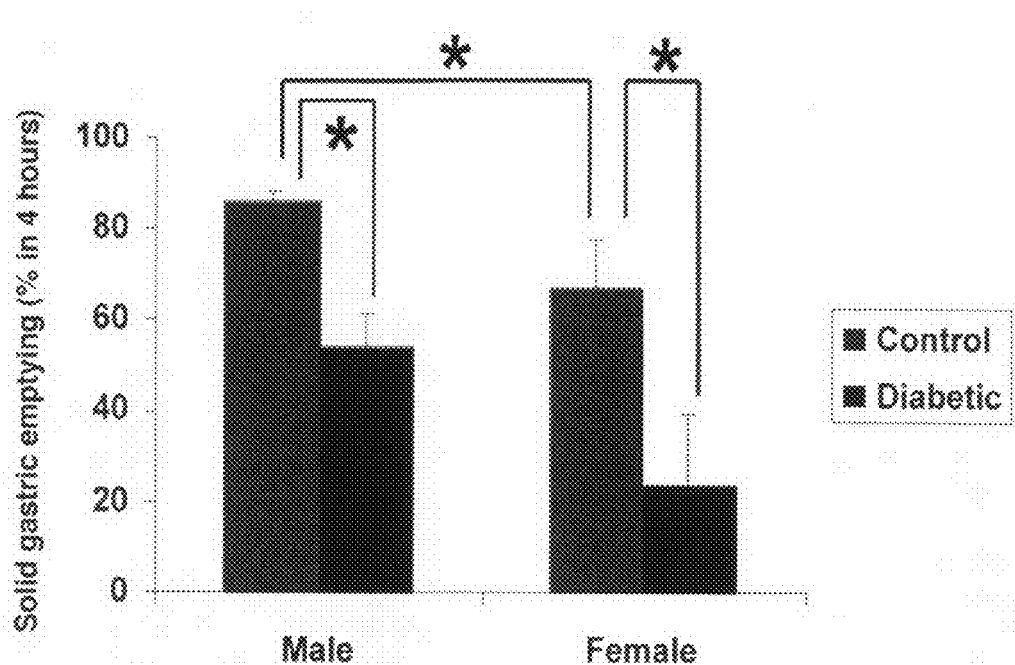
FIGS. 2A-2B show that chronic diabetes delayed solid gastric emptying in female rats.
Figure 2B:
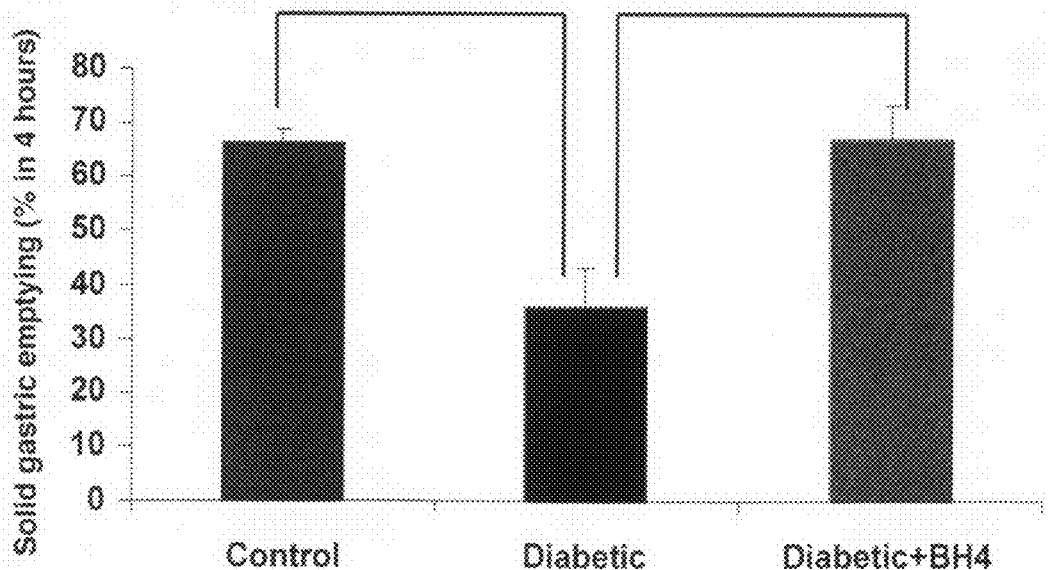

The present invention investigated whether solid gastric emptying (GE) is slower in male and female rats after diabetes induction. Additionally, whether dietary tetrahydrobiopterin attenuated the delayed gastric emptying in female diabetic rats was also examined. FIG. 1 depicts the biosynthesis of tetrahydrobiopterin. Diabetes induction significantly delayed gastric emptying in both male and female rats (FIG. 2A). However, females showed severe gastroparesis compared to males after diabetes induction. Interestingly, tetrahydrobiopterin supplementation completely restored gastric emptying in female diabetic rats (FIG. 2B).

EXAMPLE 3

Figure 3A:
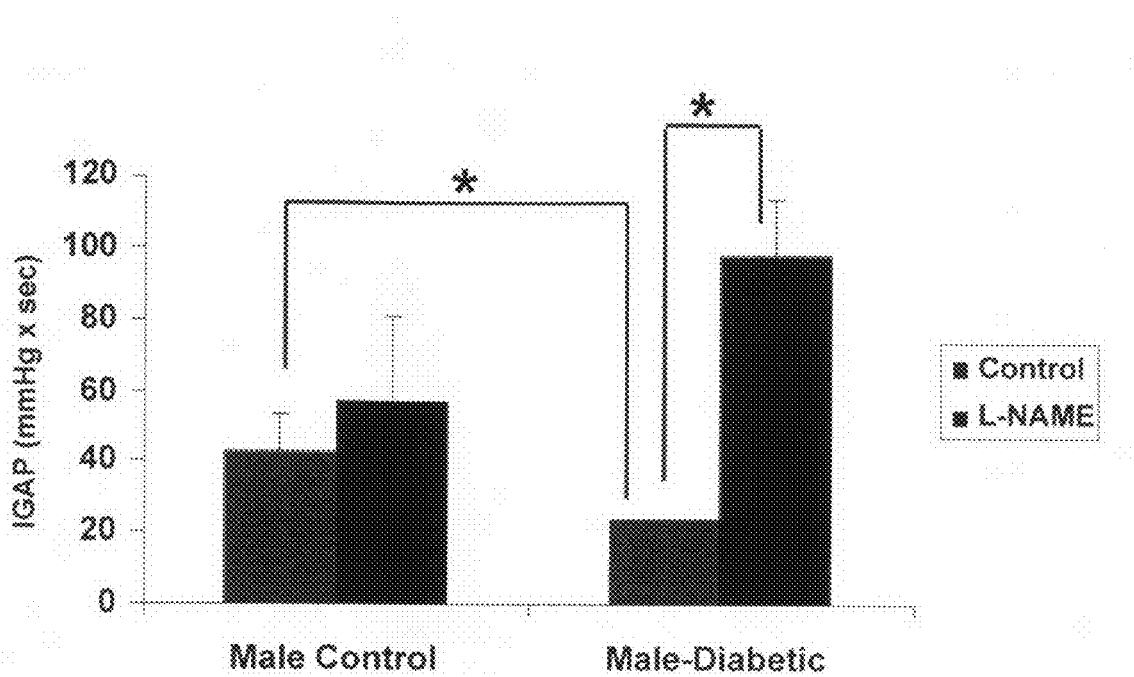
FIGS. 3A-3B show that chronic diabetes impaired intragastric antrum pressure and sensitivity to L-NAME in female rats. The intragastric antrum pressure (IGAP) was measured in normal and diabetic male (FIG. 3A) and female (FIG. 3B) rats. The transducer pressure catheter was introduced into the gastric antrum cavity 5 mm proximal to the pylorus to record IGAP (mmHgxsec). After recording the baseline IGAP, $N^G$-nitro-L-arginine methyl ester (L-NAME, 200 mg/day/kg body weight (BW)/rat) was administered subcutaneously in the same rats by osmotic mini-pumps (Alza, Palo Alto, Calif., model 2ML1 with a pumping rate of 10 µl/hour) for 4 days. All subsequent studies were performed 1 week after surgery in overnight fasted rats that were awake and in a free-moving state. Pressure recordings were performed at least 2-3 hours between 9-12 am. Bilateral ovariectomy was performed as reported previously. Dietary BH4 (25 mg/day/kg body weight (BE)/rat). *p<0.05. ANOVA.
Figure 3B:
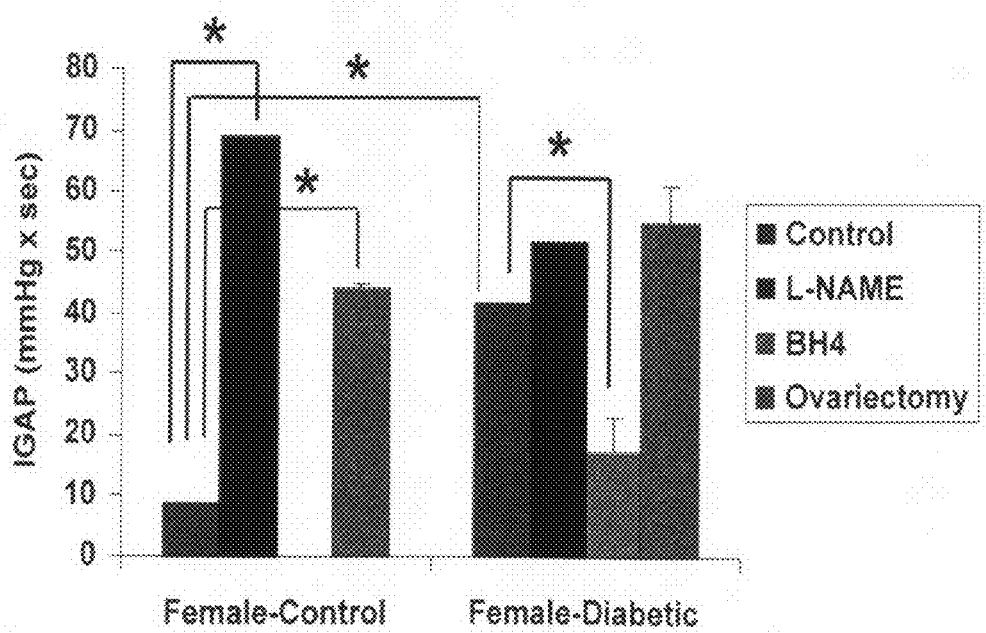

Chronic Diabetes Impairs Intragastric Antrum Pressure and Sensitivity to L-NAME in Female Rats Intragastric pressure (IGP) was measured using ambulatory telemetric device. The technique used herein is similar to that of the ambulatory manometric method used in humans to measure contractions of gastric antrum. A previous study had reported a decrease in antral contractility in women compared to age matched men by using dynamic antral scintigraphy and antriduodenal manometry. The intragastric pressure was observed herein to be lower in female compared to male rats (FIGS. 3A,3B). L-NAME treatment significantly elevated IGAP in females and this was decreased in male rats. No change in intragastric pressure was noticed with L-NAME treatment in female rats. However, males showed an increase in intragastric pressure after L-NAME treatment (FIGS. 3A-3B). Additionally, dietary tetrahydrobiopterin completely restored the elevated intragastric pressure in female diabetic rats. These observations suggested that female are more dependent on both ovarian estrogens and nitric oxide system in gastric motility functions compared to male rats. This also suggested that tetrahydrobiopterin supplementation may play a critical role in regulating nNOS activity and dimerization in female gastric tissues. The present invention contemplates investigating time dependent changes in intragastric pressure in the onset of diabetes and whether supplementation with BH4 and sex hormones restored impaired intragastric pressure in diabetic females.

EXAMPLE 4

Figure 4A:
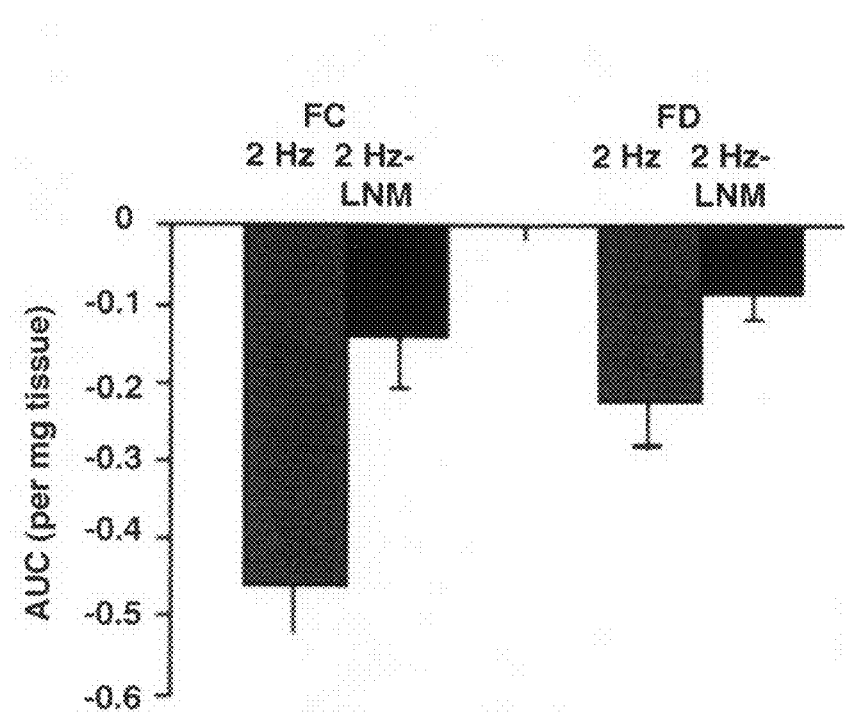
FIGS. 4A-4C show that chronic diabetes impairs nitrergic (NO produce neurons) relaxation but does not result in a loss of nitrergic neurons in female gastric tissues.
Figure 4B:
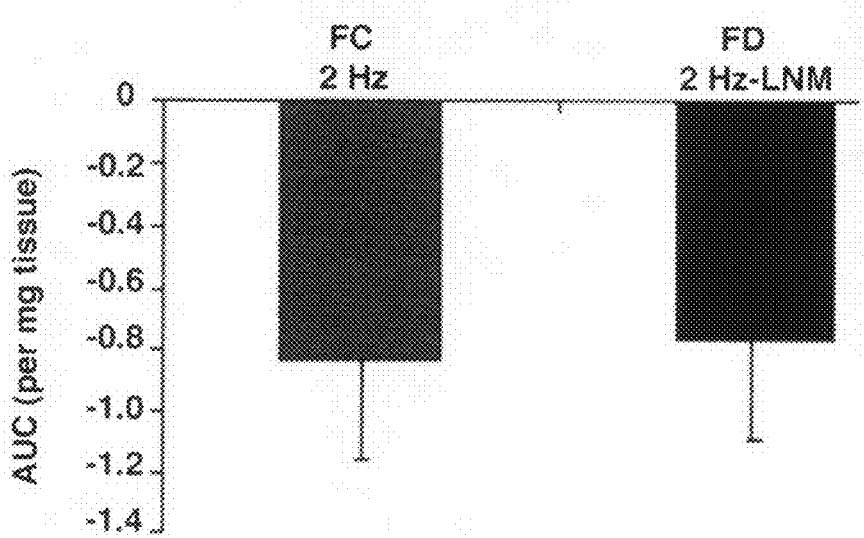

Chronic Diabetes Impairs Nitrergic (Neurons Produce NO) Relaxation in Female Gastric Tissues The nitrergic relaxation was investigated after electrical field stimulation (EFS). Gastric antrum (FIG. 4A) strips obtained from female diabetic (FD) rats showed an increase in nitrergic relaxation compared to female control (FC) group. In addition, it was also observed that preincubation with tetrodotoxin (TTX, 30 minutes, 1 μM) abolished nitrergic relaxation (data not shown). Further, the NO donor, (z)-1-[2-(2-amino ethyl)-N-(2-ammonioethyl)amino]diazen-1-ium-1,2-diolate (DETA-NONOate, 100 μM) was used to test whether the smooth muscle response to nitrergic signaling remained intact in diabetes. The data presented herein indicates that the relaxation responses to DETA-NONOate were similar in both control and diabetic gastric tissues obtained from female rats (FIG. 4B).

Thus, it appeared that females relied on nitrergic control of gastric motility to a greater extent than males and hence, were more vulnerable to alterations of this system induced by diabetes. The present invention contemplates examining the effects of diabetes, supplementation of BH4 and female sex hormones on nitrergic relaxation in female gastric fundus, antrum and pyloric LM-MP tissues.

Figure 4C:
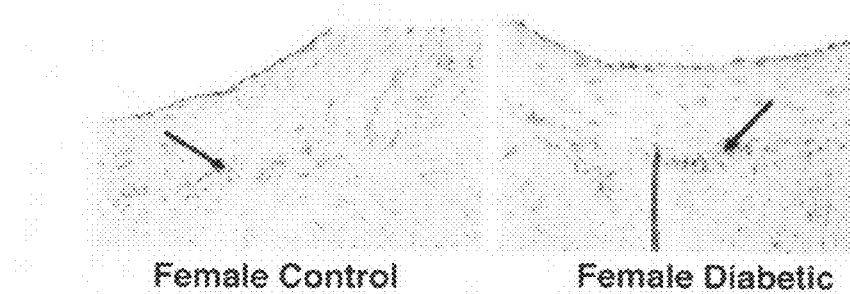

Longitudinal muscle-myenteric preparations from the stomach were utilized to examine whether nNOS containing neurons were affected by diabetes in male and female rats. Diabetes did not alter nNOS positive neurons in gastric LM-MPs compared to the control group. In addition, TUNEL staining demonstrated that chronic diabetes did not induce significant apoptosis (n=3) in either female or male diabetic gastric pyloric myenteric neurons (FIG. 4C) compared to control groups. These data suggested that the loss in nitrergic relaxation in diabetes (FIG. 4A) was not due to neuronal degeneration.

EXAMPLE 5

Chronic Diabetes does not Alter nNOS Expression in Female Gastric Tissues

Real-time RT-PCR and Western blotting studies were performed in control and diabetic female rats. It was observed that diabetes resulted in a further increase in nNOS total (COOH-terminal antibody) protein (alpha, beta and gamma) expression in female gastric tissues (FIGS. 5A-5E). Additionally, the expression of nNOS was significantly higher ($p<0.05$) in female control gastric pylorus compared to male control group. However, nNOSα protein is (NH2 terminal antibody) decreased in female diabetic gastric tissues compared to control group. These data suggested that changes in nNOSα but not total nNOS (alpha, beta and gamma) expression was critical for impaired nitrergic relaxation in diabetic gastric tissues (FIG. 4A). Based on this, it is suggested that increases observed in total nNOS protein could be due to increases in nNOS β and nNOS gamma which are not important for gastric motility functions as reported previously using nNOS knock-out mice. Hence, the present invention contemplates examining the time dependent changes in total nNOS and nNOS alpha protein expression in female gastric fundus, antrum and pyloric LM-MP tissues after diabetes induction.

EXAMPLE 6

Figure 5A:
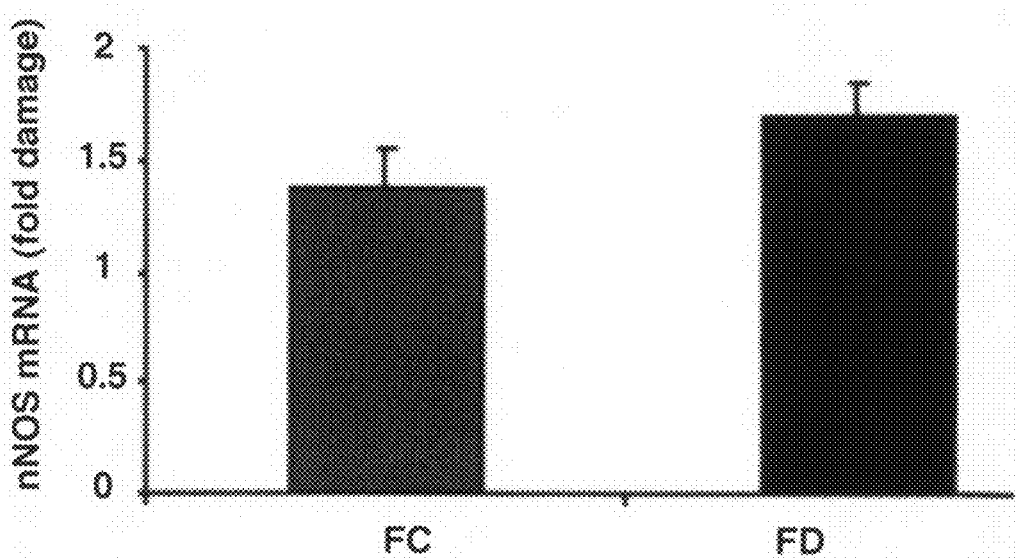
FIGS. 5A-5G show that chronic diabetes reduces nNOS-alpha protein expression in female gastric tissues. nNOS mRNA (FIG. 5A), nNOS total protein (alpha, beta and gamma, (FIGS. 5B, 5D) and nNOS alpha protein expression in female control (FC) and female diabetes (FD) (FIGS. 5C, 5E) were compared. Densitometric analysis followed by a ratio of nNOS mRNA to 18S (FIGS. 5A, 5C) or nNOS protein to β-tubulin (FIGS. 5B, 5D) were calculated. The bars represent mean±SEM. *p<0.05 FC vs FD.
Figure 5B:
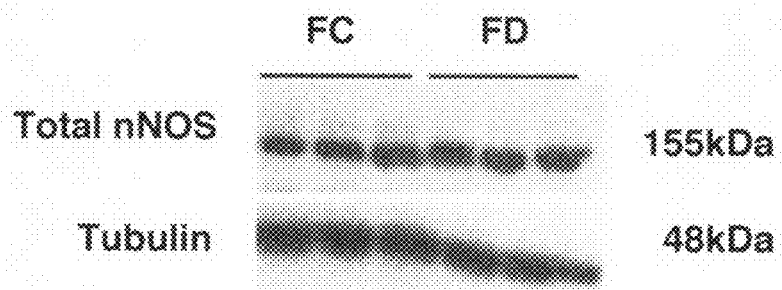
Figure 5C:
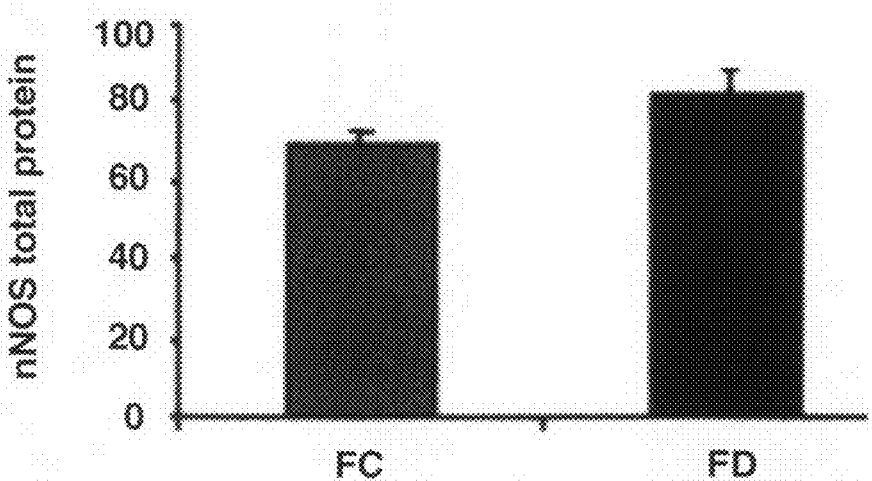
Figure 5D:
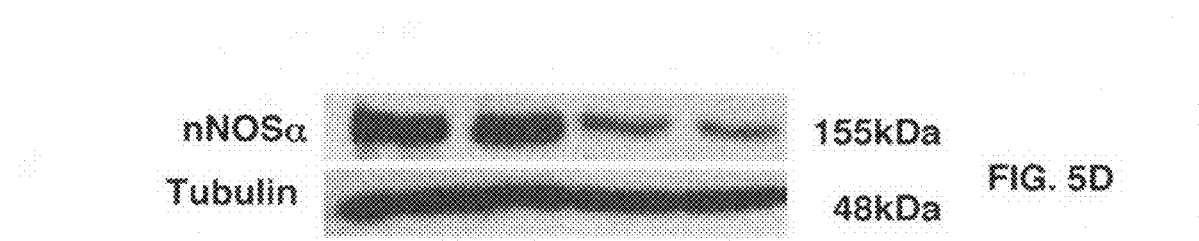
Figure 5E:
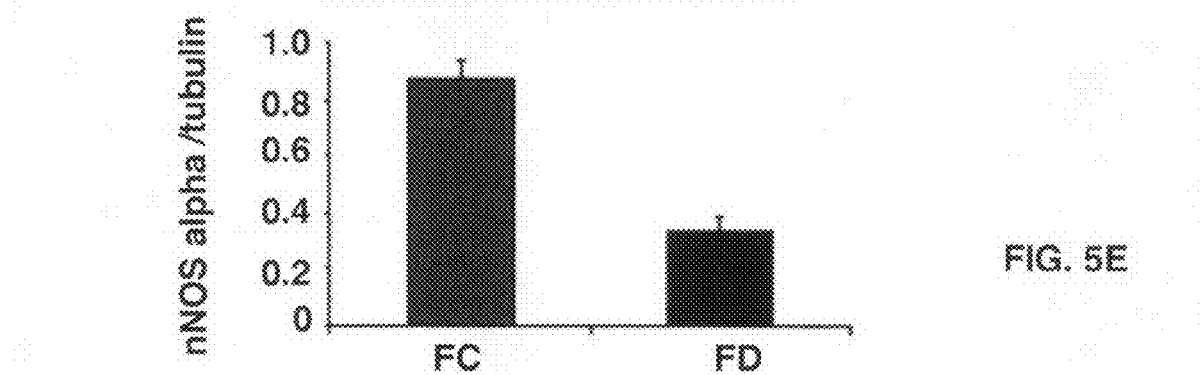
Figure 5F:
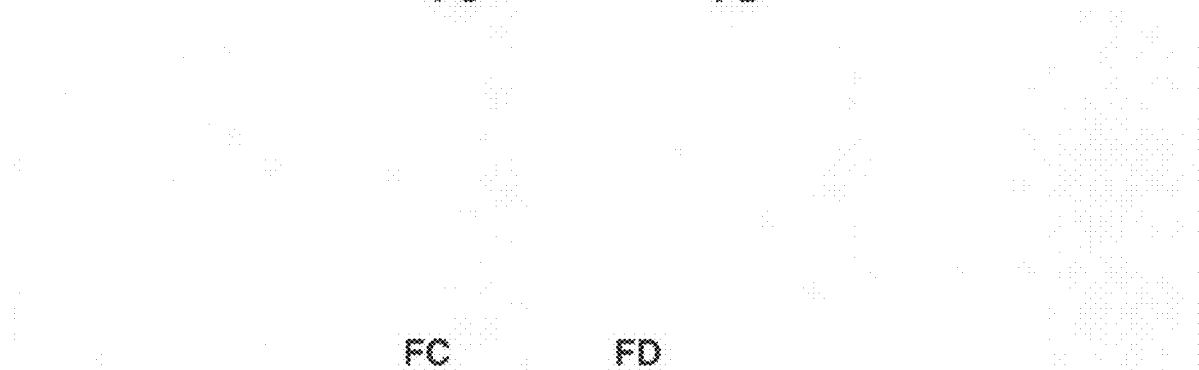
Figure 5G:
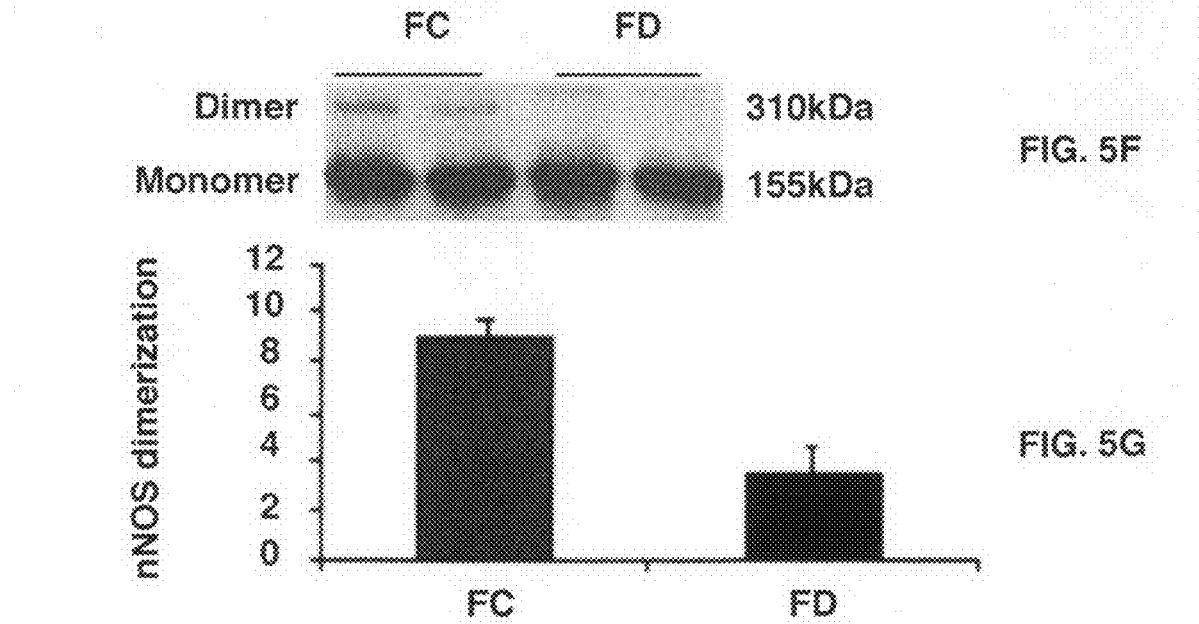

Chronic Diabetes Impairs Gastric nNOS Alpha Protein Dimerization in Female Gastric Tissue Since nNOSalpha protein expression and nitrergic relaxation are reduced in diabetic females, the changes in the dimerization state of nNOS alpha, known to be critical for the catalytic activity of the enzyme was investigated. The changes in the ratio of nNOS alpha dimers to monomers were examined using NH2-terminal antibody (derived from PDZ-GLGF domain) by low temperature SDS-PAGE. This assay is a convenient and reliable surrogate measure for the amount of stable dimer in vivo. As shown in FIGS. 5F-5G, the ratio of nNOS alpha dimer to monomer levels were significantly greater in healthy females compared to males in pyloric tissue. However, the ratio of nNOS alpha dimer to monomer levels was strikingly reduced in females on the onset of diabetes. Similar findings were noted in gastric fundus tissues. These findings suggested that the nNOS alpha dimerization and not total expression, played a critical role in modulating gastric motility functions in females. Hence, the present invention contemplates investigating the effects of diabetes and supplementation of BH4 on nNOS alpha dimerization, enzyme activity and NO production in the female gastric fundus, antrum and pyloric LM-MP tissues.

EXAMPLE 7

Chronic Diabetes Reduces NO Release in Gastric Tissues

Figure 6:
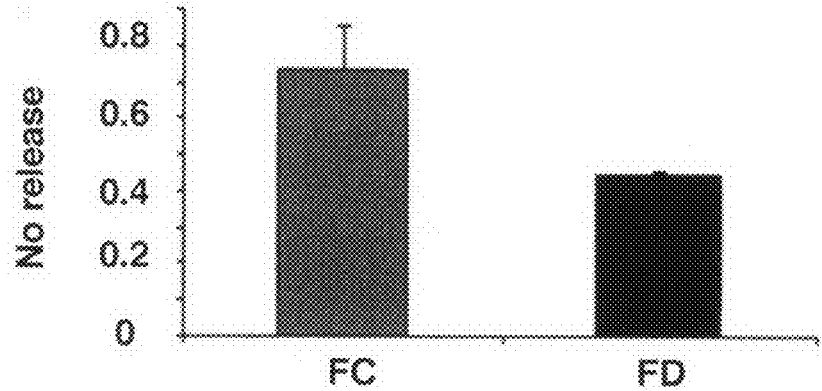
FIG. 6 shows that chronic diabetes reduces NO release in female gastric LM-MP tissues. NO release was measured by readily available kit in female control (FC) and female diabetic (FD) gastric LM-MP tissues. Mean mean±SEM, (n=3)*p<0.05.

Gastric LM-MPs were incubated for 24 hours in DMEM supplemented with 2% neurobasal medium (NB27) and 1% antibiotics. The concentration of NO (micromoles/mg tissue) was measured using readily available NO kit (Cayman corporation). As shown in FIG. 6, NO release was significantly reduced in diabetic gastric LM-MPs compared to female controls. These data suggested that decreased nNOSalpha dimerization was responsible for reduced NO release in female diabetic gastric tissues. The present invention contemplates examining whether supplementation of BH4 and female sex hormones restores reduced NO release in diabetic female gastric LM-MP tissues.

EXAMPLE 8

Chronic Diabetes Reduces BH4 Content in Gastric Pylorus Tissues

Figure 7:
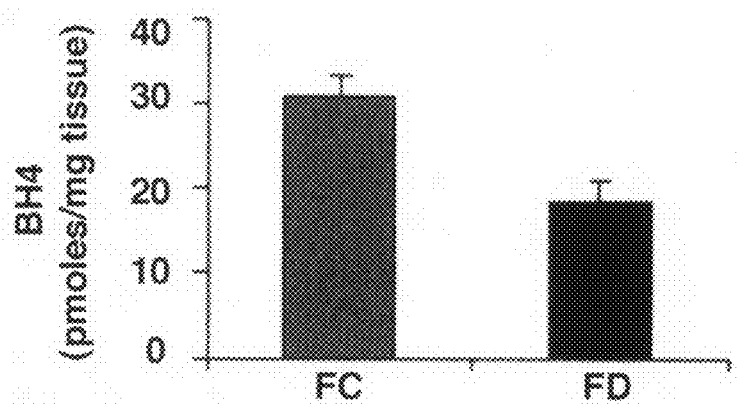
FIG. 7 shows that chronic diabetes reduced BH4 content in gastric pylorus tissues. BH4 levels were measured by HPLC in female control (FC) and female diabetic (FD) gastric pylorus tissues. mean±SEM, (n=3), *p<0.05.

The concentration of tetrahydrobiopterin in female control and diabetic gastric pylorus tissues were measured using high performance liquid chromatography (HPLC). As shown in FIG. 7, significant ($p<0.05$) reduction in tetrahydrobiopterin content was seen in gastric tissues obtained from female diabetic rats. These studies suggested that nNOS alpha but not other proteins play a central role in the relaxation of the pyloric sphincter and circular smooth muscles in females. The present invention contemplates examining whether supplementation with BH4 and female sex hormones restores these effects.

EXAMPLE 9

Inhibition of BH4 Synthesis Reduces Nitrergic Relaxation in Gastric Tissue

Both nitrergic relaxation and nNOS alpha dimerization were decreased in gastric fundus of diabetic female rats compared to control group. Thus, whether the inhibition of endogenous tetrahydrobiopterin biosynthesis by DAHP (an inhibitor of GTPCH1) impaired the nitrergic function in the normal female gastric fundus was examined.

Figure 8:
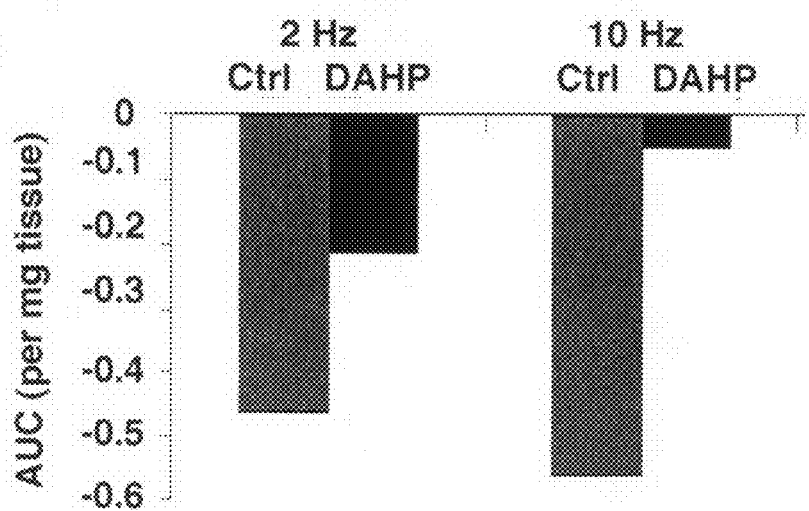
FIG. 8 shows effect of endogenous BH4 inhibition by DAHP (10 mM, 3 hour incubation) on nitrergic function (n=2). Basal tone relaxation studies in gastric tissues were performed after EFS stimulation at 2 and 10 Hz (n=2). In vitro treatment with DAHP, reduced nitrergic relaxation after EFS stimulation. AUC=area under curve.

As shown in FIG. 8, in vitro incubation with the GTPCH1 inhibitor, DAHP (10 mM, 3 hours incubation), inhibited nitrergic relaxation in female control gastric tissues (n=2). Thus, the present invention contemplates examining whether in vivo supplementation of tetrahydrobiopterin restores nNOS dimerization, enzyme activity, NO production and thus, nitrergic function in the female diabetic gastric fundus, antrum and pylorus LM-MP tissues.

EXAMPLE 10

Figure 9A:
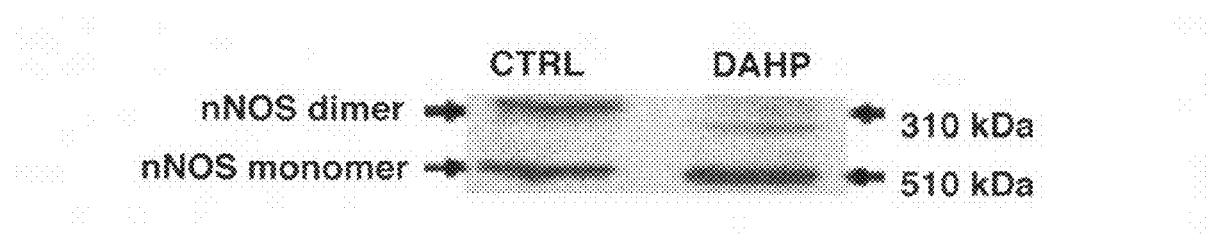
FIGS. 9A-9C shows in vitro effects of DAHP, an inhibitor for GTPCHI (first and rate limiting enzyme in BH4 biosynthesis) on nNOS dimerization and NO release in healthy female rat gastric LM-MPs. Gastric LM-MPs were incubated for 48 hrs in the presence or the absence of DAHP (10 mM) and nNOS dimerization (FIG. 9A-9B) in tissues and NO release (FIG. 9C) in the media were assessed. (n=3).
Figure 9B:
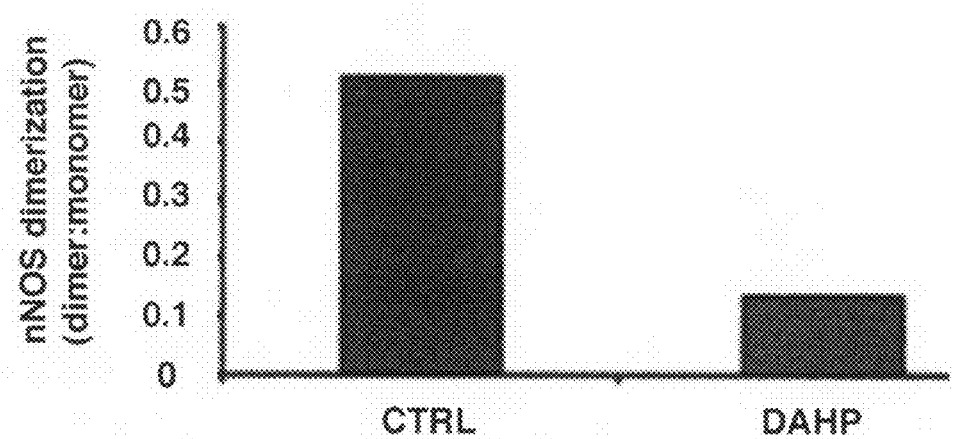
Figure 9C:
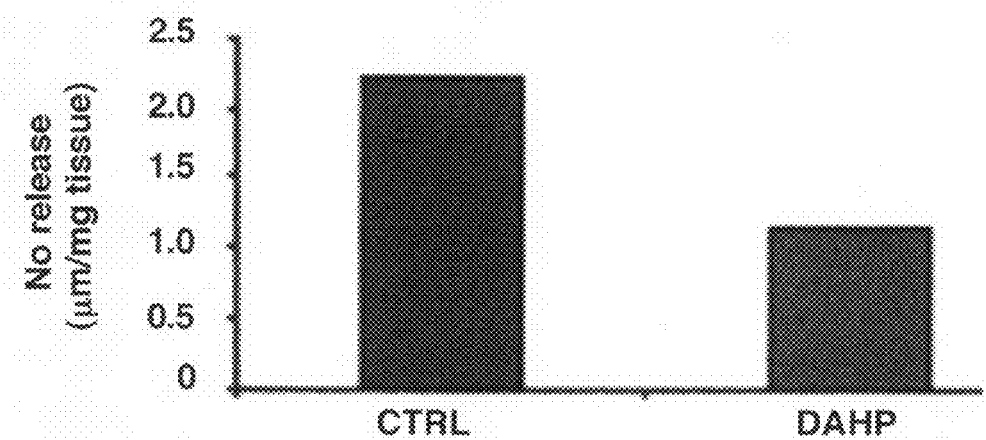

Inhibition of BH4 Synthesis Reduces nNOS Dimerization and NO Release in Gastric Tissue The present invention examined whether treatment with DAHP in vitro uncoupled gastric nNOS dimerization and NO release in healthy female rats. Gastric longitudinal muscle-myenteric plexus (LM-MP) were incubated for 48 hours in the presence or absence of DHAP (10 mM). It was observed that inhibition of BH4 biosynthesis with DAHP decreased both nNOS dimerization (FIGS. 9A-9B) and NO release (FIG. 9C). These additional data further support the hypothesis that impaired biosynthesis of gastric BH4 accounts for the decrease in nNOS activity and nitrergic relaxation in female diabetic gastroparesis.

EXAMPLE 11

Chronic Diabetes Reduces GTPCH1 Expression in Female Gastric Tissues

Figure 10A:
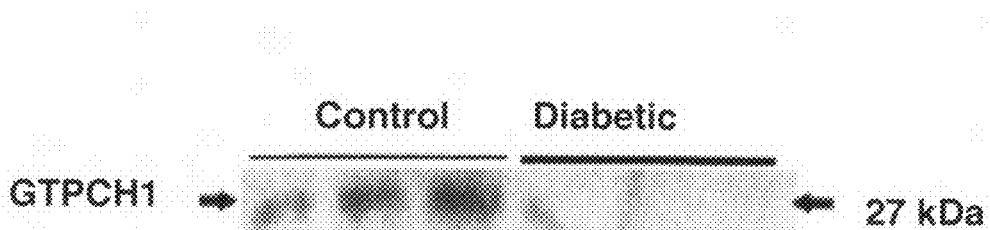
FIGS. 10A-10B show the effect of chronic diabetes on GTPCH1 protein expression in rat female stomachs (n=3), *p<0.05.
Figure 10B:
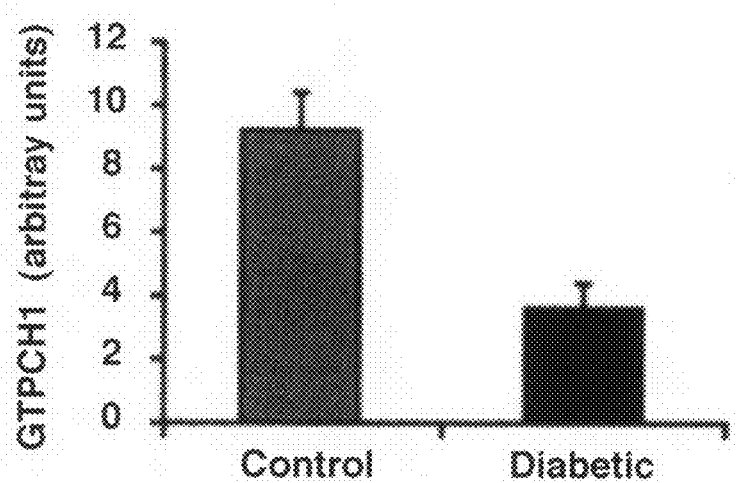
Figure 11:
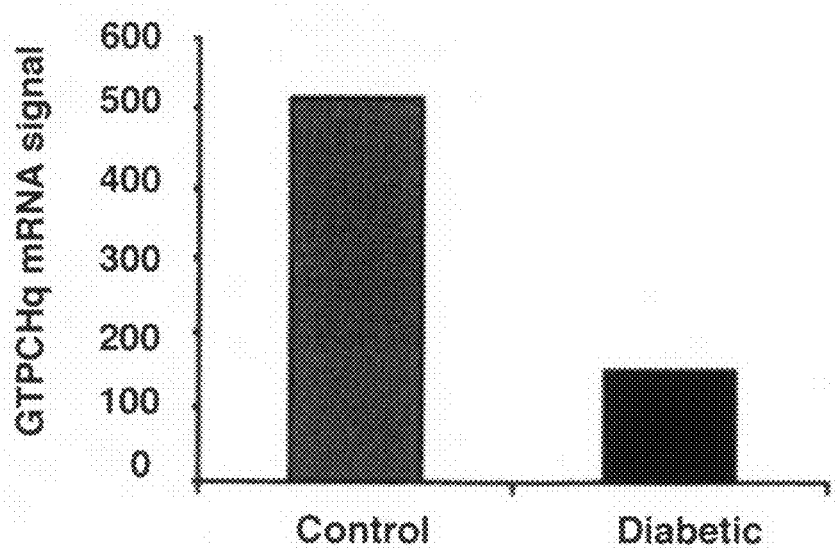
FIG. 11 shows effect of chronic diabetes on GTPCH1 mRNA levels in female patients. GTPCH1 protein expression was reduced in female diabetic patient gastric biopsies. Full thickness gastric biopsies were used for Affymetric gene arrays (n=2).

GTPCH1 is the rate limiting enzyme in biopterin (BH4) synthesis. As shown in FIGS. 10A-10B, GTPCH1 protein expression was significantly (p<0.05) decreased in stomachs of diabetic females (n=3). In a separate set of experiments, full thickness of gastric biopsies obtained from female patients with chronic diabetic gastroparesis was examined. Additionally, GTPCH1 mRNA levels, as measured by Affymetrix gene arrays, were substantially lower in gastric tissues of diabetic women than in controls (n=2, FIG. 11). Hence, the present invention contemplates investigating whether the GTPCH1 expression (mRNA and protein) and BH4 levels were altered in the female diabetic gastric fundus, antrum and pyloric LM-MP tissues.

EXAMPLE 12

Figure 12A:
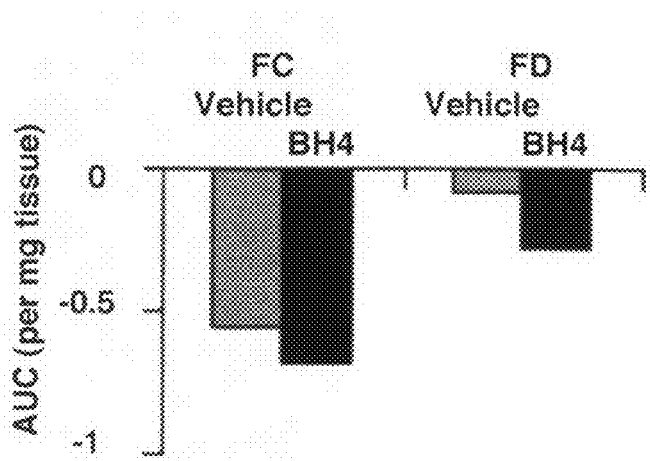
FIG. 12A-12C show that supplementation of dietary BH4 improves solid gastric emptying, nNOS activity and nitrergic relaxation in female diabetic gastric fundal tissues.
Figure 12B:
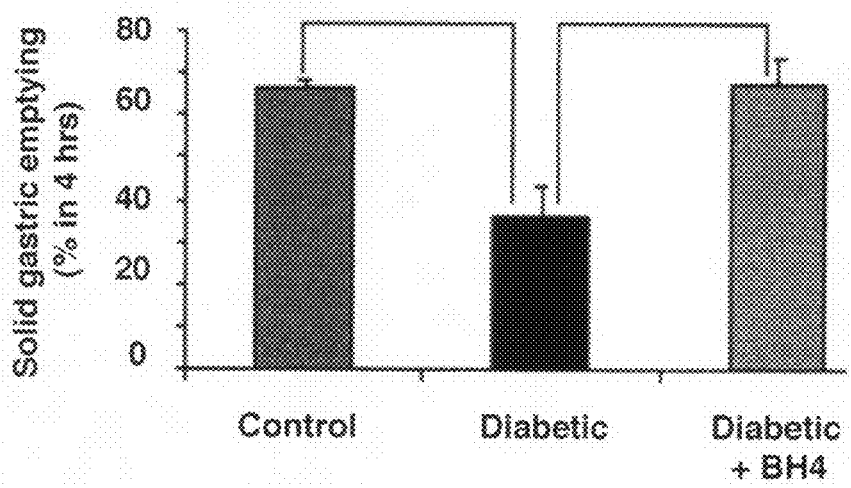
Figure 12C:
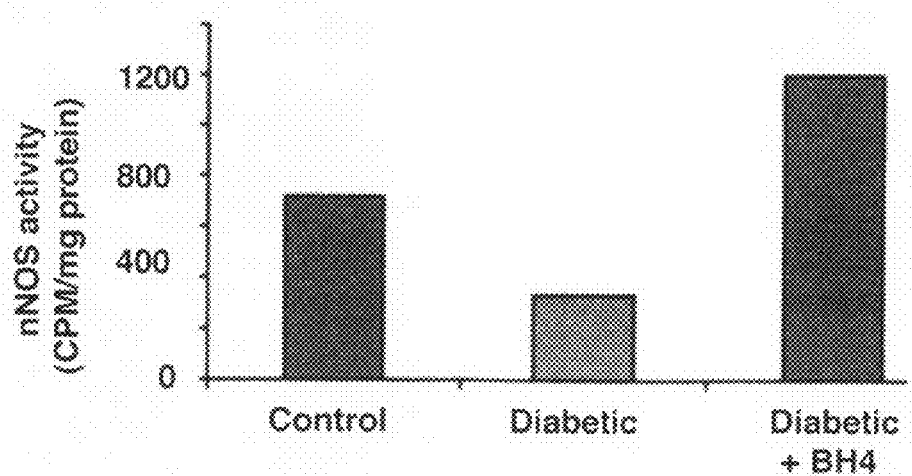

BH4 Supplementation Improves Solid Gastric Emptying, nNOS Activity and Nitrergic Relaxation in Female Diabetic Gastric Fundal Tissues As shown in FIG. 12A, exogenous tetrahydrobiopterin (100 μM, 30 min incubation) increased nitrergic relaxation in diabetic (FD) but not control (FC) female stomachs (n=2, FIG. 12A). BH4 supplementation beginning from either day 1 (FIG. 12B) or 3 weeks (p=0.007) after diabetes induction significantly restored delayed gastric emptying for solids in female diabetic rats (FIG. 12C). Hence, tetrahydrobiopterin might play a critical role in NO mediated gastric motility and that a reduction in tetrahydrobiopterin synthesis might lead to gastric dysmotility in females. The present invention contemplates investigating whether oral supplementation of tetrahydrobiopterin or sepiapterin attenuate the impaired nNOS dimerization, enzyme activity, NO production and nitrergic relaxation in female diabetic gastric fundus, antrum and pylorus LM-MP tissues and restore the delayed gastric emptying in diabetic females.

EXAMPLE 13

Figure 13A:
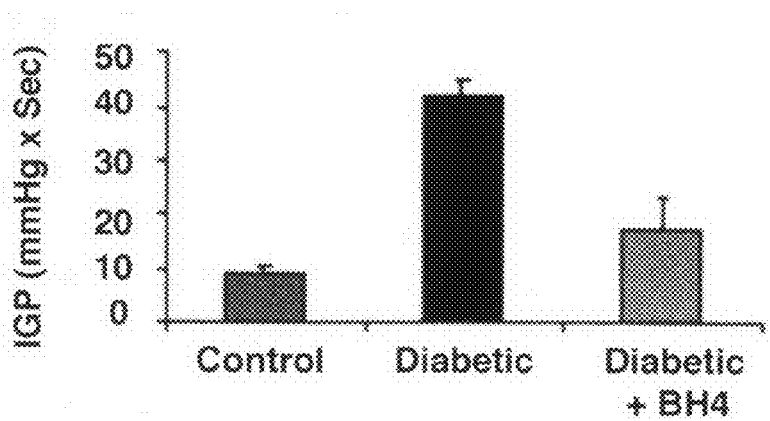
FIGS. 13A-13C show that supplementation with dietary BH4 improves intragastric pressure, nNOSalpha protein expression in female diabetic gastric tissues.
Figure 13B:
Figure 13C:
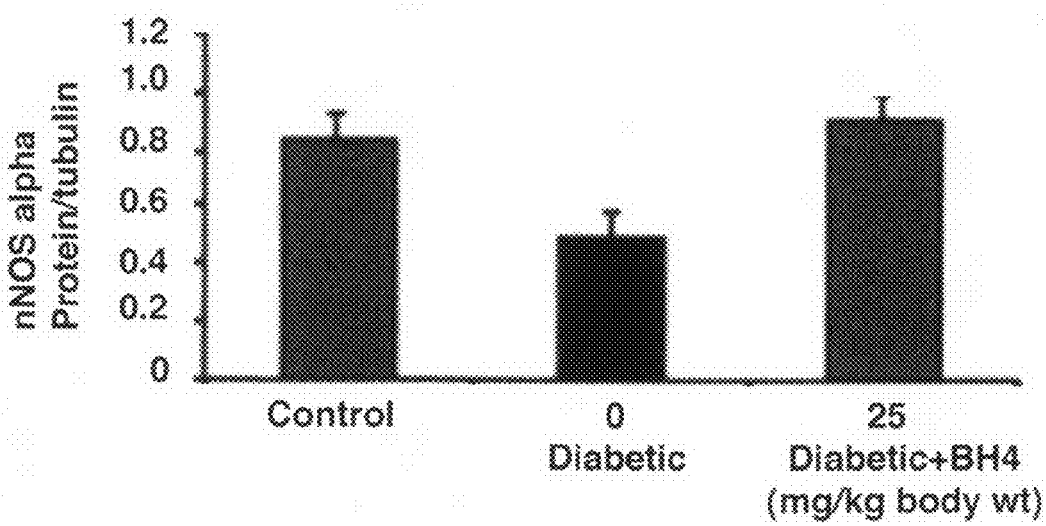

Supplementation of Dietary BH4 Improves Intragastric Pressure, nNOSalpha Protein Expression in Female Diabetic Gastric Tissues Dietary BH4 (25 mg/kg b.w/rat/day) was supplemented for female rats for 12 weeks beginning from day 2 after diabetic induction. Intragastric pressure (IGP) was measured in female control, diabetic and diabetic+BH4 treated rats. As shown in FIG. 13A, supplementation of BH4 significantly attenuated increased IGP in diabetic female rats. In another experiment, diabetic females were treated for 3 weeks with BH4 and nNOS alpha protein expression was measured in treated and untreated gastric tissues. Diabetes, significantly decreased nNOSalpha protein expression and BH4 supplementation attenuated this (FIGS. 13B-13C). The above data strongly suggest that the gastric motility functions in females are primarily dependent on nitrergic mechanism and a decrease in BH4, a cofactor for nNOS function, may lead to altered IGP and delayed gastric emptying in diabetic females.

EXAMPLE 14

Estradiol-17Beta Delays Gastric Emptying for Solids in Healthy Females

Figure 14:
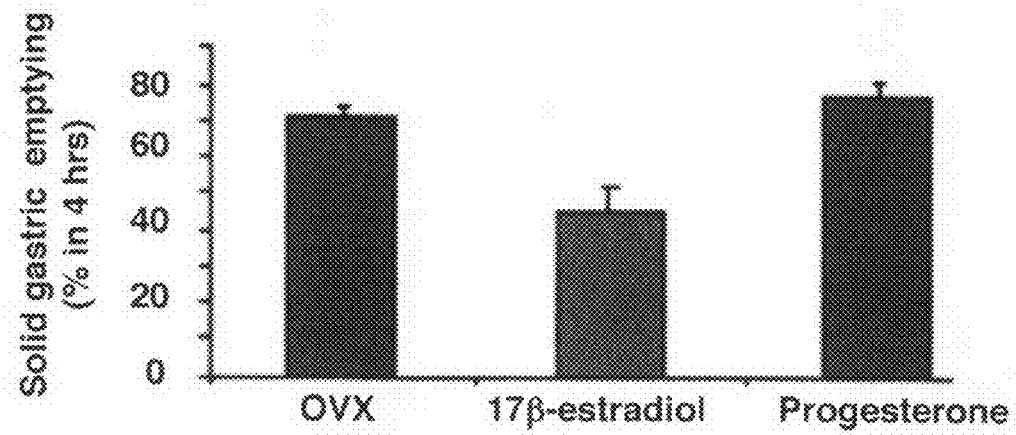
FIG. 14 shows that estradiol-17beta delays gastric emptying for solids in healthy females. The OVX female animals were implanted subcutaneously (per kg body weight) with 21 day release of either Estradiol-17beta (E2; 2 mg), P4 (20 mg) or placebo (control) pellets. Solid gastric emptying was then assessed. Data were mean±SEM, n=3-4. *p<0.05 compared to control group.

Ovariectomized (OVX; removal of estrogen and progesterone) rats were treated either with estradiol-17beta ($E_2$) or progesterone ($P_4$) for three weeks and solid gastric emptying was assessed as reported previously. $E_2$ but not $P_4$ significantly delayed gastric emptying for solids in female rats (FIG. 14). These studies together with animal (94) and clinical studies suggest that gastric emptying is slower in women compared to men and elevated levels of serum $E_2$ may play a critical role in this condition.

EXAMPLE 15

Figure 15:
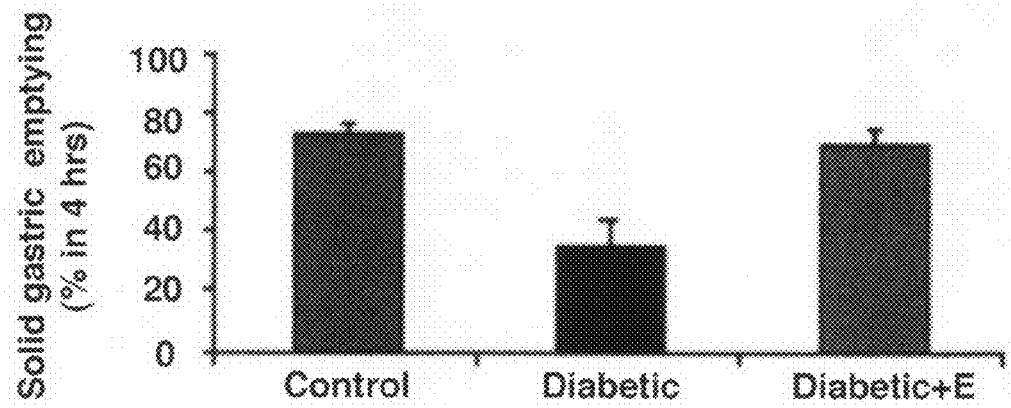
FIG. 15 shows that chronic diabetes delayed gastric emptying in female rats. Estradiol-17 beta (E2, 2 mg/kg b.w/21 days) treatment reversed delayed gastric emptying in diabetic females. Data were mean±SEM, n=3-4. *p<0.05.

Estradiol-17Beta Accelerates Gastric Emptying for Solids in Chronic Diabetic Female Rats It has been demonstrated that sex steroid hormones, $E_2$ and $P_4$ are significantly reduced in STZ-induced diabetic rats and that $E_2$ treatment restored diabetes induced nephropathy in female rats. In the present invention, female rats were treated with $E_2$ for 3 weeks beginning from day 2 after diabetes induction. As shown in FIG. 2, diabetes significantly delayed gastric emptying for solids. Treatment with $E_2$, significantly restored delayed solid gastric emptying in diabetic female rats (FIG. 15). These data suggest that diabetes results in decrease in estrogen levels as reported earlier. Supplementation of exogenous estrogens accelerated the delayed gastric emptying in diabetic rats. The data from FIGS. 2A-2B suggest that endogenous estrogens regulate gastric motility in both health and diabetic state.

EXAMPLE 16

Chronic Diabetes Reduces ER-Alpha Expression in Diabetic Female Gastric Tissues

Figure 16:
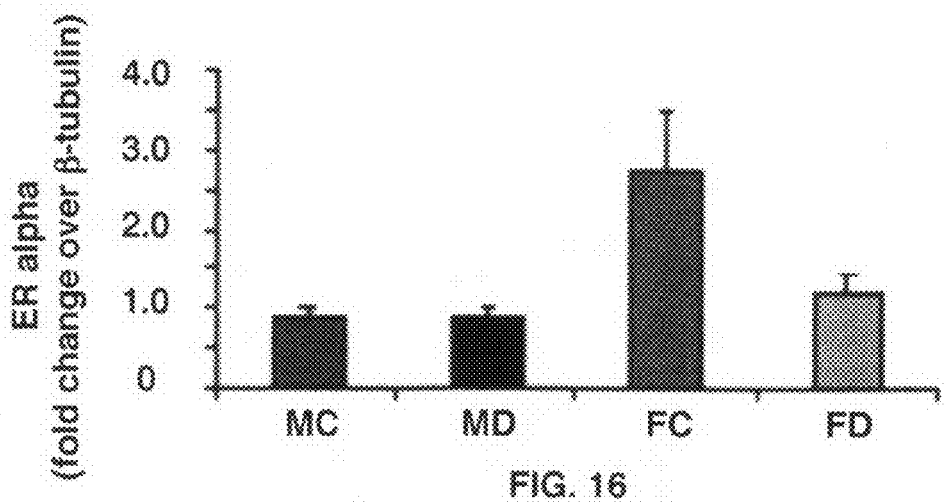
FIG. 16 shows effect of chronic diabetes on estrogen receptor alpha (ER-alpha) mRNA in male and female rat stomachs. MC, male control; FC, female control; MD, male diabetic; FD, female diabetic. n=3-4, *p<0.05 compared to MC, $p<0.05 compared to FC.

Sex steroid hormones, E2 and P4 are significantly reduced in STZ-induced diabetic rats. Both estrogen receptor (ER) subtypes (alpha & beta) are primarily localized in gastric myentric neurons in rats. Real time-PCR studies after normalizing with beta tubulin (neuronal marker) indicate that significant increases in ER-alpha mRNA were noticed in female control (FC) compared to male control (MC) group (FIG. 16). In addition, significant (p<0.05) reduction in ER-alpha mRNA was noticed in gastric tissues obtained from female but not male diabetic rats.

EXAMPLE 17

Figure 17A:
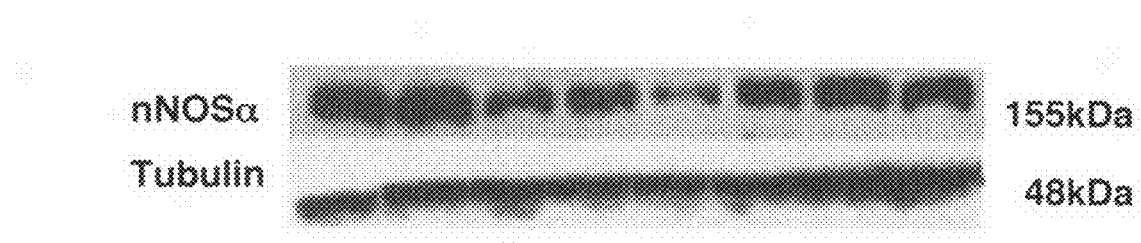
FIGS. 17A-17B show that Estradiol-17beta restores reduced nNOSalpha protein expression in diabetic female rat gastric tissues. The diabetic female animals were implanted subcutaneously (per kg b.w) with 21 day release of E2 (2 mg) or placebo (control) pellets. nNOSalpha protein expression was then measured. Data were mean±SEM, n=3. *p<0.05 compared to control group.
Figure 17B:
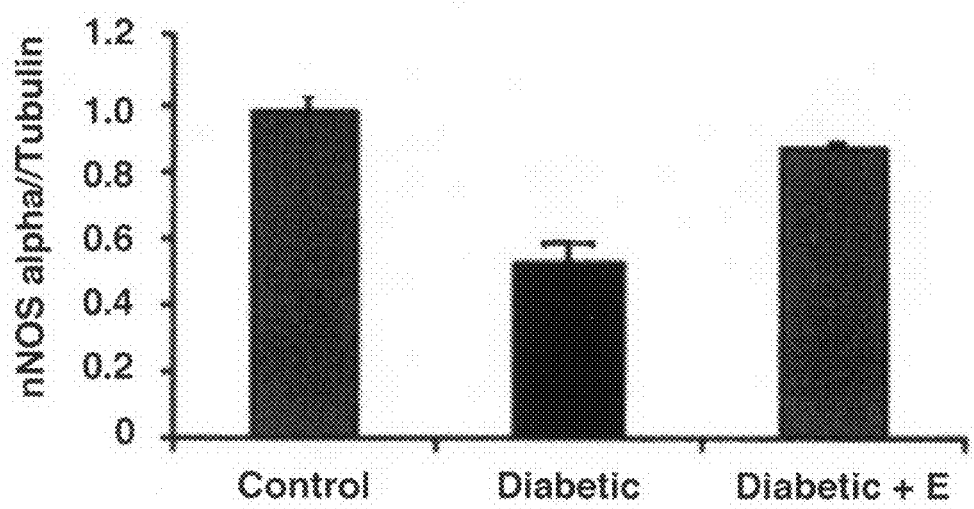

Estradiol-17Beta Restores Reduced nNOSalpha Protein Expression in Diabetic Female Rat Gastric Tissues As shown in FIGS. 17A-17B, chronic diabetes reduced nNOSalpha protein expression in female rat gastric tissues. Further, it was shown for the first time that $E_2$ treatment, significantly restored nNOSalpha protein expression in diabetic female rat gastric tissues. The present invention contemplates examining whether $E_2$, $P_4$ or $E_2+P_4$ treatment restores impaired BH4 and nitrergic systems in diabetic female rat gastric tissues.

EXAMPLE 18

BH4 Decreases the Levels of TNF Alpha in Female Diabetic Rat Circulation

The level of TNF alpha in the circulation of diabetic female rat was examined after and before administration of tetrahydrobiopterin. It was observed that tetrahydrobiopterin decreased elevated TNF-alpha levels in the circulation of diabetic female rat. It is hypothesized that the elevated TNF-alpha might be involved in altering nitric oxide, free radical and NF-kB levels and causing gastroparesis in diabetic patients. The present invention contemplates examining the role of TNF alpha in diabetic gastroparesis.

EXAMPLE 19

Chronic Diabetes Decreases nNOS Activity, Nitrergic Relaxation, Expression of GTPCH1 and BH4 Content in the Female Rat Gastric Tissues The present invention contemplates examining whether diabetes alters nNOS expression, dimerization, nNOS activity, NO production and nitrergic relaxation in the female rat gastric fundus, antrum and pylorus LM-MPs. Briefly, diabetes is induced by streptozotocin injection (STZ, 55 mg/kg body weight) in female (7 week old) Sprague Dawley rats. Control groups receive vehicle only (citrate buffer, pH 4.0). Both control and diabetic rats are selected during the diestrous stage of the estrous cycle. Animals are sacrificed by decapitation after 12 weeks of diabetes. Gastric fundus, antrum and pylorus longitudinal muscle-myenteric plexus (LM-MP) tissues are collected, snap frozen and saved in $-80°$ C. for biochemical analysis. nNOS mRNA is analyzed using Real-Time PCR. An optimal treatment regimen is determined for maximum nNOS expression in all regions of gastric LM-MP tissues in addition to NO levels. NH2-terminal polyclonal antibody derived from PDZ/GLGF motif (1-195 amino acids, Zymed Corporation, CA) is used to determine the active (dimers) and inactive (monomers) forms of nNOS alpha using low temperature SDS-PAGE in non-boiled samples. The COOH-terminal antibody is used for nNOS total protein expression.

The activity of nNOS from gastric LM-MPs is analyzed as the rate of conversion of L-(U-14C)-arginine to L-(U-14C)-citrulline. Nitrergic relaxation is assessed in gastric fundus, antrum and pylorus LM-MPs after transmural stimulation (electrical field stimulation, EFS) at various frequencies (1 Hz, 2 Hz, 5 Hz, 10 Hz) in vitro. NO dependent relaxation is confirmed by preincubating the tissues for 30 minutes with L-NAME ($10^{-4}$M) or nNOS selective inhibitor (TRIM, $10^{-4}$M). In some experiments, the tissues are incubated for 30 minutes with tetrodotoxin (TTX, 1 μM) to determine whether nitrergic mediated relaxation is influenced by ENS. For examining the NO production, all regions of gastric LM-MPs are incubated in serum free neurobasal medium for 24 to 48 hours and media is collected for determination of total nitrites by a commercially available nitrite assay kit.

Additionally, whether chronic diabetes impairs the tetrahydrobiopterin biosynthetic pathway in female diabetic gastric fundus, antrum and pyloric LM-MPs is also examined herein. Briefly, the control and diabetic female rats (discussed supra) are sacrificed and their blood is collected to determine the levels of circulatory tetrahydrobiopterin and total biopterin (BH4, BH2, B). Gastric fundus, antrum and pyloric LM-MP tissues are collected, snap frozen and saved in $-80°$ C. The GTPCH1 mRNA expression, the protein and the enzyme activity is measured by Real time RT-PCR, Western Blotting and HPLC, respectively. Additionally, the total biopterin (BH4, B2 and B) and ratio of total versus tetrahydrobiopterin content is measured by HPLC.

EXAMPLE 20

BH4 and/or Sepiapterin Supplementation Restores Impaired Gastric nNOS Alpha Dimerization, NO Synthesis and Nitrergic Relaxation in Diabetic Female Rat Gastric Tissues.

Dietary tetrahydrobiopterin or sepiapterin (2.5, 10 or 40mg/day/Kg body weight) are administered to groups of diabetic female rats from day 1 until 12 weeks after diabetes induction by streptozotocin. The control group received similar diet composition without tetrahydrobiopterin or sepiapterin. Tetrahydrobiopterin or sepiapterin (purchased from Swerick Laboratories, Switzerland) was compressed into rodent rat chow pellets (TestDiet, Land O'lakes, Purina Feed, LLC, Richmond, Ind.) without addition of water or heating to prevent oxidation of the compound. The concentration of tetrahydrobiopterin or sepiapterin in the pellets is calculated to provide a required dose (2.5, 10 or 40 mg) per kilogram body weight daily. Pellets are stored at $-20°$ C. After the treatment periods, the total nNOS expression (mRNA, protein), nNOS alpha dimerization, enzyme activity and NO production in gastric fundus, antrum and pyloric LM-MPs is quantitated.

The effect of dietary tetrahydrobiopterin or sepiapterin on nitrergic relaxation is examined in all regions of female gastric tissues. Organ bath studies is performed herein. Nitrergic relaxation is demonstrated after transmural stimulation at various frequencies (1 Hz, 2 Hz, 5 Hz, 10 Hz) and NO-dependent relaxation is confirmed by preincubating gastric tissues with L-NAME (100 μM) or nNOS selective inhibitor (TRIM, 100 μM). Additionally, the GTPCH1 mRNA, protein, enzyme activity, BH4 content and total biopterins is measured. The BH4 and sepiapterin dose and time regimens is selected to mimic the endogenous concentration range.

EXAMPLE 21

Supplementation of SEP on Blood Glucose and Body Weight in Female Diabetic Rats

Table 1 demonstrates whether supplementation of sepiapterin attenuated the elevated blood glucose and reduced body weights in female rats after diabetes induction. A significant weight loss (174.3±4.8) was noted in the diabetic rats compared to age-matched control group (255.9±2.3). Supplementation of sepiapterin had no significant effect (188±4.3) on the diabetes-induced body weight loss. Fasting blood glucose levels were significantly elevated in female rats (521.3±35.01 mg/dl) after diabetes induction (Table 1). Blood glucose levels were unchanged with sepiapterin in both control as well as diabetic female rats.

TABLE 1

Blood glucose level and body weight in the control and diabetic female rats

|  | Control (C) | C + SEP | Diabetes | DB + SEP |
|---|---|---|---|---|
| Body Weight, g | 255.9 ± 2.3 | 242 ± 7.7 | 174.3 ± 4.8* | 188 ± 4.3* |
| Blood Glucose mg/dl | 102 ± 3.2 | 112 ± 1.0 | 521.3 ± 35.01* | 494.5 ± 13.96* |

EXAMPLE 22

Attenuation of Diabetes-Induced Solid Gastric Emptying by SEP in vivo

Figure 18:
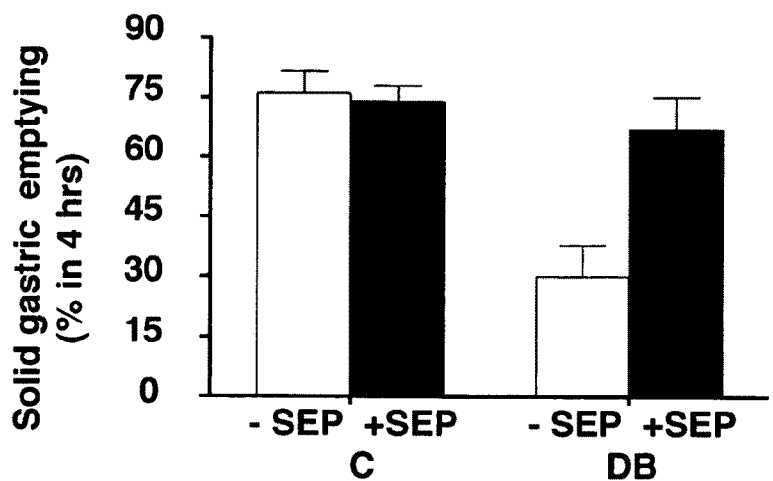
FIG. 18 shows the effect of sepiapterin (SEP) treatment on diabetes-induced solid gastric emptying in female rats. Groups (4-6) of diabetic rats were received dietary sepiapterin (20 mg kg$^{-1}$ body wt) daily for 10 days after diabetic induction with single injection of STZ (55 mg kg$^{-1}$ body wt; ip). Control group was injected with vehicle (9 mmol citrate buffer) only. The values are mean±SE for 4-6 animals. Statistical significance was determined by Tukey test after one-way ANOVA. *p<0.05 compared with control group; #p< compared with DB group.

FIG. 18 shows the effect of sepiapterin supplementation on solid gastric emptying (% in 4 h) in female diabetic rats. A significant reduction (30.0±8.0) in the solid gastric emptying was observed in diabetic rats compared to control (76.0±5.6). According to FIG. 18, sepiapterin supplementation did not affect the solid gastric emptying in control rats (74±4), whereas, a significant induction (67.0±8.2) in the solid gastric emptying was observed when diabetic animals were supplemented with sepiapterin. The underlying mechanisms for this effect was explored, beginning with changes in gastric antrum nitrergic relaxation and NO release.

EXAMPLE 23

Effect of SEP on Nitrergic Relaxation in vivo

Figure 19:
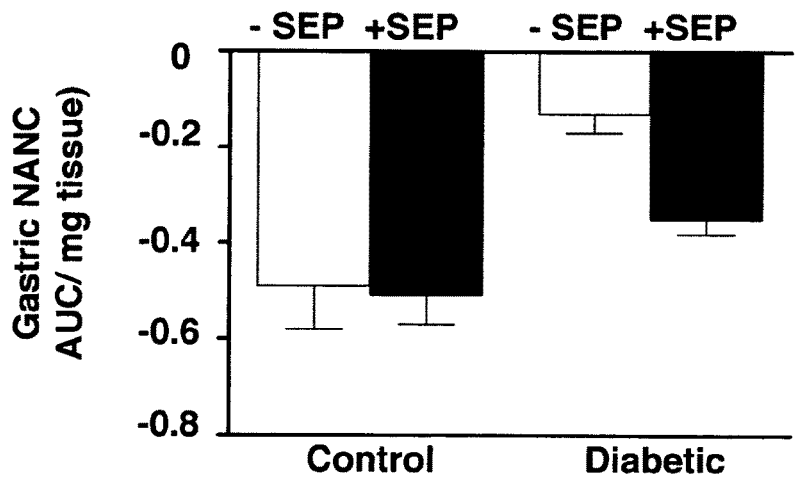
FIG. 19 shows the effect of sepiapterin on nitrergic relaxation in diabetic rat gastric muscular tissues in vivo. Nitrergic relaxation was measured following daily exposure to dietary sepiapterin (20 mg kg$^{-1}$ body wt) for 10 days after diabetic induction with single injection of STZ (55 mg kg$^{-1}$ body wt ip). Control group was injected with vehicle (9 mmol citrate buffer) only. Values are mean±SE (N=4-6). Statistical significance was determined by Tukey test after one-way ANOVA. *p<0.05 compared with control group; #p< compared with DB group.

The effects of sepiapterin on diabetic-induced induction of nitrergic relaxation in gastric antrum muscle strips from female rats following EFS (2 Hz) are presented in FIG. 19. Induction of diabetes caused a 3.8-fold decrease (−0.13±0.04) in the nitrergic relaxation compared with control rats (−0.49 ±0.09). Supplementation of sepiapterin resulted in almost complete reversal (−0.35 ±0.03) of diabetes-induced alteration of nitrergic relaxation. However, no change in nitrergic relaxation was noticed in control rats treated with sepiapterin (−0.51 ±0.06).

The underlying mechanisms for this effect was examined, beginning with changes in nNOSalpha structure and function which was previously shown to be profoundly affected in diabetes. To show that these changes in nNOSalpha expression and structure were of functional significance further experiments in vitro and in vivo were performed.

EXAMPLE 24

Figure 20A:
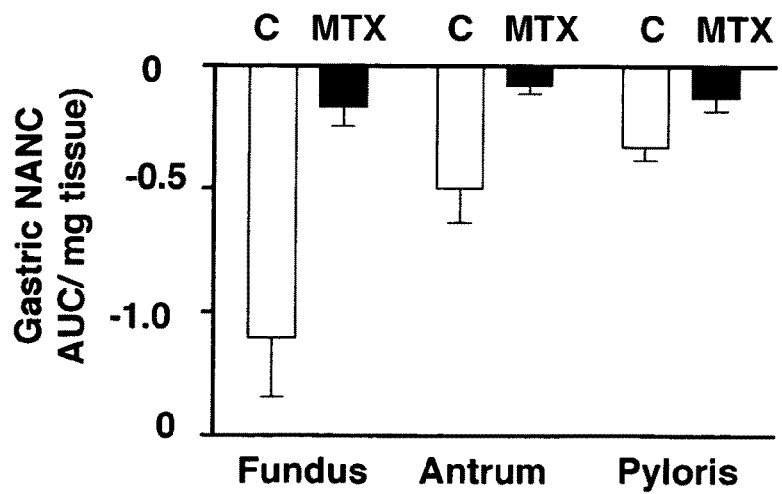
FIGS. 20A-20D show the effect of methotrexate.

Effects of in vivo MTX Treatment on Nitrergic Relaxation and nNOSalpha Dimer Expression An inhibitor of $BH_4$ biosynthesis, MTX, was used to analyze the role of $BH_4$ or sepiapterin on NO production in gastric tissue. MTX inhibits the enzyme DHFR and decreases the availability of $BH_4$ via salvage pathway. To demonstrate the role of sepiapterin in stomach function, the effect of MTX was measured on the nitrergic relaxation in vivo. According to FIG. 20A, gastric tissue from control healthy female rats exhibited substantial relaxation following EFS (2 Hz) (fundus: −1.1±0.24; antrum: −0.5±0.14; pylorus: −0.33±0.05). MTX treatment significantly decreased the nitrergic relaxation in all areas of gastric muscular tissues (fundus: −0.17±0.076; antrum: −0.08±0.04; pylorus: −0.13±0.05).

Figure 20B:
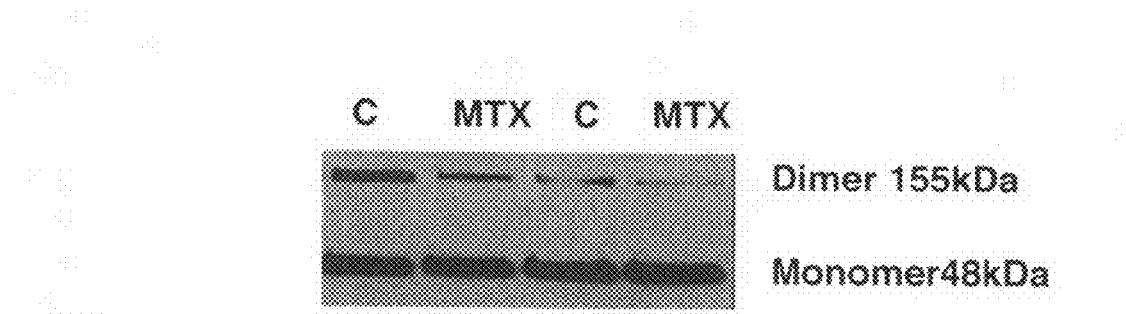
Figure 20C:
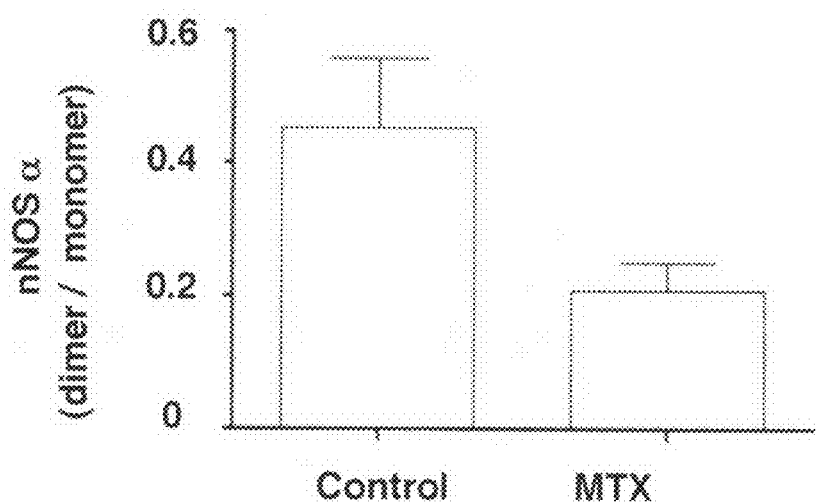

To measure nNOSalpha dimer/monomer levels in MTX treated rats, the dimerization study was performed by LT-PAGE gel. FIGS. 20B-20C shows a significant decrease in the dimer/monomer ratio in MTX treated group (0.2±0.04) when compared to control group (0.45±0.2).

EXAMPLE 25

Figure 20D:
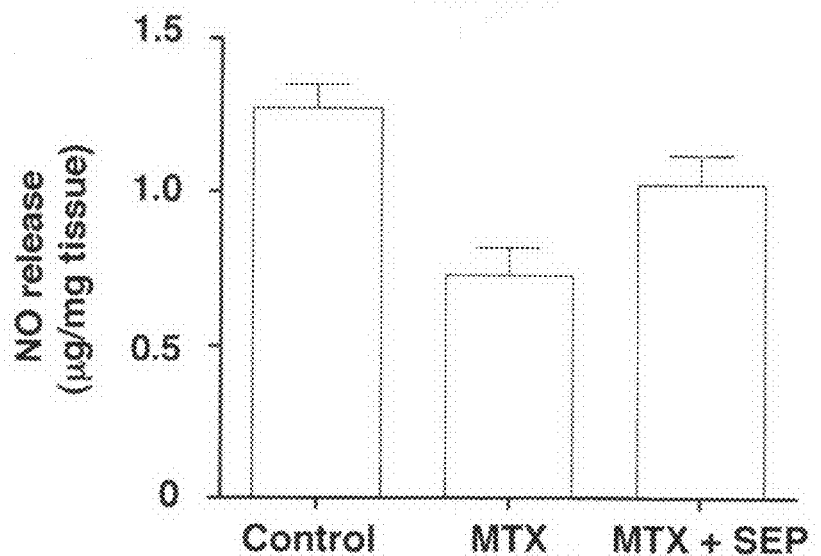

Effect of MTX and SEP Supplementation on Gastric NO Release in Female Diabetic Rats In Vitro To examine whether the NO production is dependent on SEP pathway, NO release in MTX treated gastric antrum muscle strip was demonstrated. MTX exposure caused a significant decrease ($p<0.05$) in NO release in vitro (FIG. 20D). Inhibition of DHFR, the critical enzyme for the production of $BH_4$ in salvage pathway, significantly reduced nitrergic relaxation in healthy rats (1.28±0.08 vs 0.73±0.15). MTX-induced decrease in NO release was attenuated by SEP treatment (1.02±0.19).

EXAMPLE 26

Effect of SEP on nNOSalpha Protein Expression and nNOSalpha Dimerization

Figure 21A:
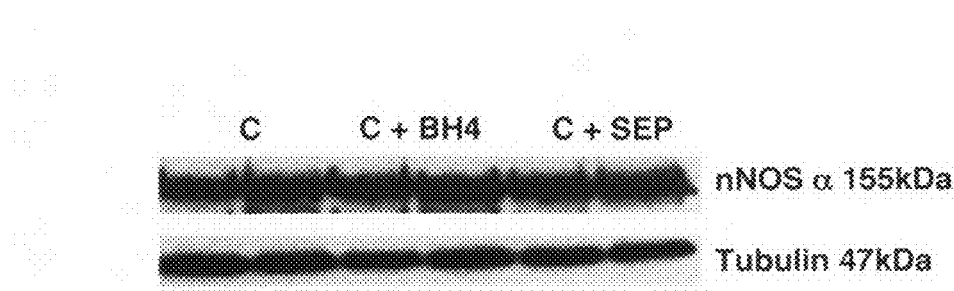
FIGS. 21A-21H shows the effect of sepiapterin on nNOSalpha protein expression and nNOSalpha dimerization of diabetic rat gastric tissues. nNOSalpha protein expression and nNOSalpha dimerization was measured following either daily exposure to sepiapterin (20 mg kg$^{-1}$ body wt) for 10 days or BH$_4$ supplementation (20 mg kg$^{-1}$ body wt per day) for 2 weeks after diabetic induction with single injection of STZ (55 mg kg$^{-1}$ body wt ip). Control group was injected with vehicle (9 mmol citrate buffer) only.
Figure 21B:
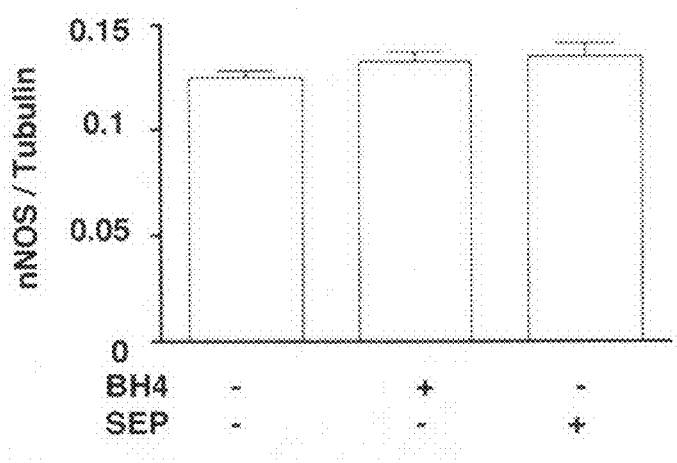
Figure 21C:
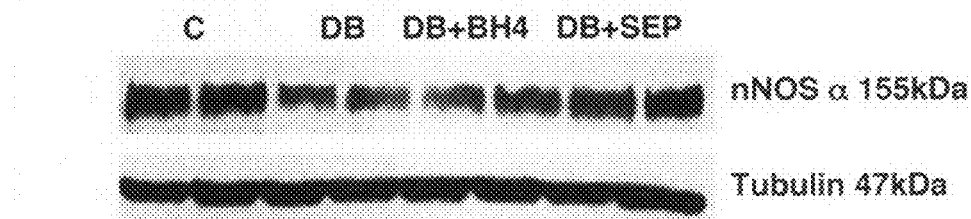
Figure 21D:
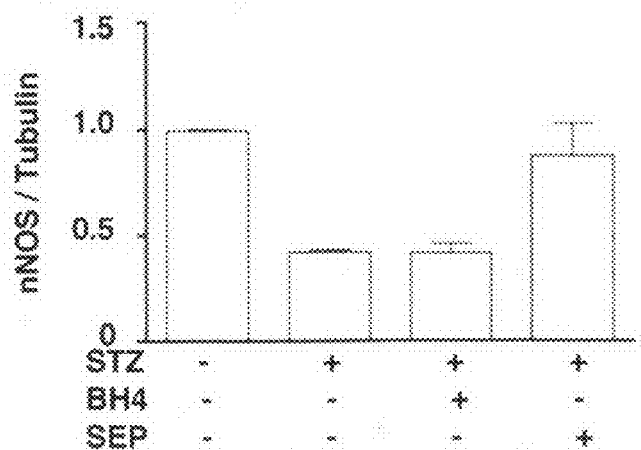

According to data presented in FIGS. 21C-21D, the protein level of nNOSalpha, the only functional isoform of nNOS in gastric antrum tissue was significantly decreased (0.42±0.01) following 9 weeks of diabetes. Supplementation of sepiapterin to diabetic female rats results in significant restoration of nNOSalpha protein level (0.88±0.15), whereas supplementation of $BH_4$ for two weeks did not alter the nNOSalpha protein level (0.42±0.05). However, no change in nNOSalpha protein expression was observed when control rats treated with either $BH_4$ or sepiapterin (FIGS. 21A-21B).

Figure 21E:
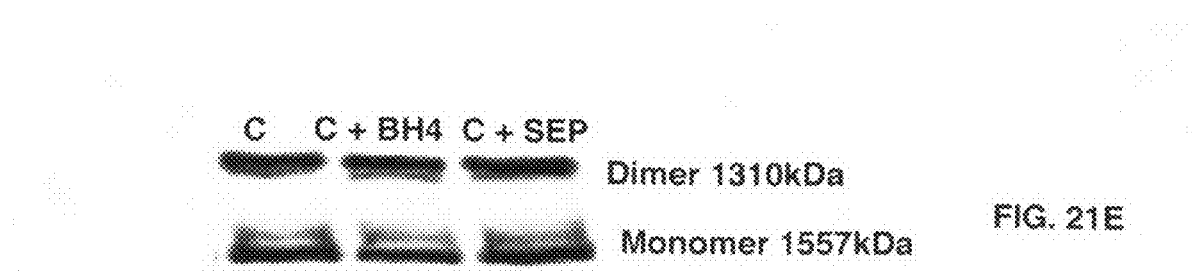
Figure 21F:
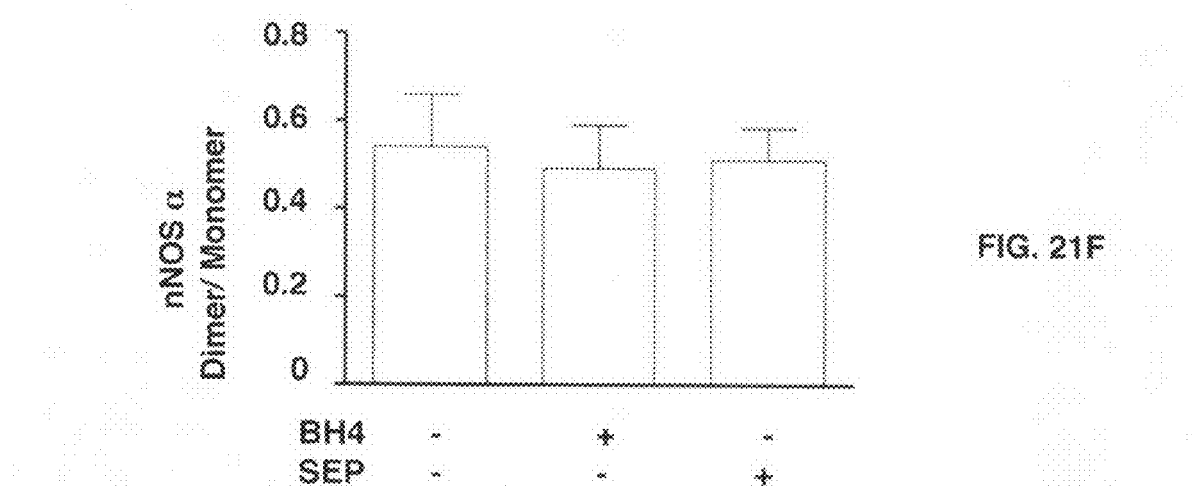
Figure 21G:
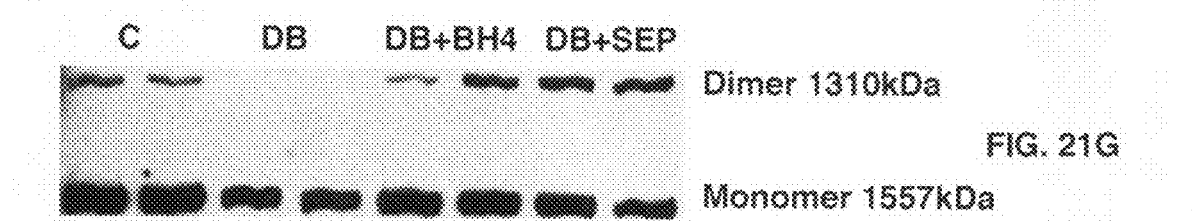
Figure 21H:
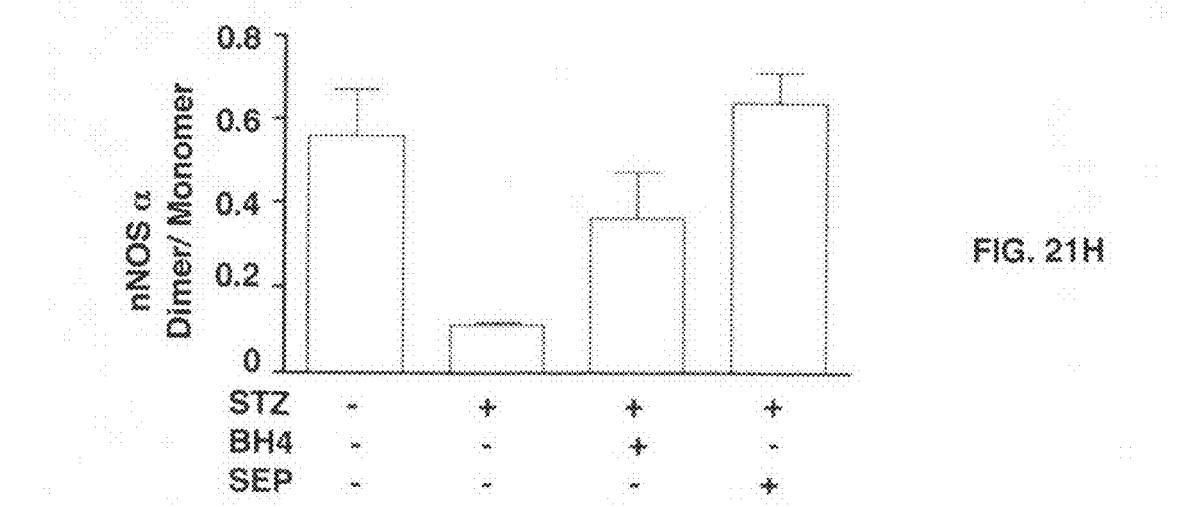

To measure whether decrease in the gastric antrum nNOSalpha was the result of altered nNOSalpha dimer levels in diabetic rats, the dimerization study was performed by LT-PAGE gel. As depicted in FIGS. 21E-21F, a significant decrease in the gastric antrum nNOSalpha dimer/monomer ratio was seen in diabetic female rats compared to control (0.11±0.01 vs 0.56±0.11). Supplementation of sepiapterin resulted in complete reversal of diabetes-induced alteration of nNOSalpha dimmer/monomer level (0.64±0.07). Though two weeks of $BH_4$ supplementation did not change the nNOSalpha protein level (FIGS. 21C-21D), it significantly increased the nNOSalpha dimmer/monomer level (0.36±0.11) compared with diabetes-induced female rats (FIGS. 21G-21H).

The present study established that sepiapterin treatment attenuated delayed solid gastric emptying in diabetic female rats. In this study, it was also demonstrated that 25 supplementation of sepiapterin prevented the down regulation of both nNOSalpha protein level as well as dimmer/monomer level in diabetic female rats. This result suggests that increased gastric dysfunction in diabetic rats is restored by sepiapterin or BH4 treatment.

In diabetic gastroparesis, delayed gastric emptying generally results from impaired phasic antral contractions, tonic motor defects, and increased liquid retention in the fundus. Another reason of delayed emptying is increased outflow resistance in the pylorus and abnormal pyloric contraction. It has been reported earlier that diabetic induction causes differences in nitrergic regulation of gastric motility associated with the reduction in gastric emptying.

Sepiapterin can serve as a $BH_4$ precursor and is metabolized in mammalian cells by sepiapterin reductase to $BH_2$. Though sepiapterin is not considered a physiologic metabolite in humans or animals, it has been used as an exogenous source. (28). $BH_4$ deficiencies have been associated with diabetic complications (29). $BH_4$ is essential for NOS to synthesize NO. Low $BH_4$ levels impair the production of NO, and leads to increased superoxide radical production, due to nNOS uncoupling. The superoxide radical then reacts with NO resulting into the production of peroxynitrite. This further reduces biological availability of NO.

This information provides a rational basis for the use of supplemental sepiapterin in diabetic conditions. Supplementation of sepiapterin can normalize the delayed gastric emptying associated with diabetes in female rats. This is in good agreement with the showing that supplementation of $BH_4$ restored the delayed gastric emptying associated with diabetes in female rats. This results are further supported by attenuation of diabetes induced altered nitrergic relaxation in vivo.

nNOS, which produces NO, is an important neuronal enzyme. NO can serve as a neuromodulator in a second messenger system for neuron-to-neuron communications. It has been well known that $BH_4$, a critical cofactor for NOS activity, acts as a redox switch in the oxygenase domain of NOS. In this study, nitrergic relaxation as well as nNOSalpha dimerization was affected significantly by MTX in healthy female rats and sepiapterin restored the NO production. These results revealed that $BH_4$ biosynthesis is regulated not only by the main de novo pathway but also by the salvage pathway. These findings suggest a potential strategy for reducing NO production in vivo.

Induction of diabetes reduced the expression of nNOSalpha protein in pylorus. This notion was further evident by the reductions in the dimmer level of nNOSalpha and supplementation of dietary $BH_4$ for 3 weeks stabilizes the functionally active, dimeric form of nNOSalpha in pylorus. $BH_4$ also inhibits monomerization of nNOS, as well as the inactivation of the enzyme. The present results demonstrate that induction of diabetes causes decrease in both nNOSalpha monomer and dimmer levels, which has been restored by $BH_4$ or SEP treatment in gastric antrum. It is possible that sepiapterin or $BH_4$ may protect degradation of enzyme as well as improve the stabilization of nNOS dimmer and activity of the enzyme.

In addition to the de novo biosynthesis of $BH_4$, mammalian cells can also generate $BH_4$ by an alternate pathway where sepiapterin is converted to $BH_4$ by sepiapterin reductase and DHFR. Cellular $BH_4$ levels have been increased both in vitro and in vivo by exogenous supply of $BH_4$ via salvage pathway. Sepiapterin treatment may selectively reverse the effect of diabetes by enhancing the intracellular $BH_4$ that helped preserve the nNOS dimmer level. Although the current study did not report that sepiapterin treatment increase $BH_4$, either increase in the intracellular $BH_4$ level and/or because of the change in the ratio of $BH_2/BH_4$ by sepiapterin may prevent NOS uncoupling, resulting in restoration of appropriate NOS activity, nitrergic relaxation and gastric emptying.

Thus, sepiapterin or $BH_4$ offer a protection against diabetes-induced activation of gastric motility. Sepiapterin can move across the cell membrane in both an inward and outward direction. $BH_4$, however, is virtually unable to cross the cell membrane in either direction. The two successive reactions, sepiapterin to $BH_2$, and $BH_2$ to $BH_4$, favor production of $BH_4$ due to cellular redox-homeostasis. Sepiapterin is enforcedly taken up by the cell and $BH_4$ is accumulated in the cytosol in a continuous fashion. This is in agreement with the current findings such that 10 day treatment with sepiapterin restored nitrergic function. Taken together, both $BH_4$ as well as SEP may be more effective therapeutic reagents in the treatment of diabetes induced gastric dysfunction.

In summary, the present data suggests that impaired bioavailability of NO may be associated with decreased $BH_4$ biosynthesis via salvage pathway. Supplementation of sepiapterin accelerated gastric emptying and gastric nNOSalpha expression as well as nNOSalpha dimerization.

The following references were cited herein:
1. Soykan et al., Dig Dis Sci 43, 2398-2404 (1998).
2. Camilleri M., Rev Gastroenterol Disord 2, 47-56 (2002).
3. Bityutsky et al., Am J Gastroenterol 92, 1501-1504 (1997).
4. Bell et al., South Med J 95, 1297-1299 (2002).
5. Revicki et al., Qual Life Res 13, 833-844 (2004).
6. Parkman et al., Gastroenterology 127, 1592-1622 (2004).
7. Rayner and Horowitz, Nat Clin Pract Gastroenterol Hepatol 2, 454-462, (2005).
8. Coleski et al., J Pharmacol Exp Ther 312, 103-111 (2005).
9. Ishiguchi et al., Am J Physiol Gastrointest Liver Physiol 279, G740-7 (2000).
10. Mizuta et al., Am J Physiol 277, G275-279 (1999).
11. Martinez-Cuesta et al., Br J Pharmacol 114, 919-924 (1995).
12. Takahashi T., J Gastroenterol 38, 421-430 (2003).
13. Nakamura et al., J Clin Invest 101, 1479-1489 (1998).
14. Nakao et al., J Physiol 507 (Pt. 2), 549-560 (1998).
15. Patil et al., Indian J Exp Biol 43, 167-171 (2005).
16. Kim et al., J Pharmacol Sci 92 337-347 (2003).
17. Shah et al., Am J Physiol regul Integr Comp Physiol, 279, R1478-1485 (2000).
18. Huang et al., Cell 75, 1273-1286 (1993).
19. Mashimo et al., Gastroenterology, 119, 766-773 (2000).
20. Undeland et al., Neurogastroenterol Motil 9, 19-24 (1997).
21. Undeland et al., Dig Dis Sci 41, 9-16 (1996).
22. Huber et al., Am J. Physiol., 275, G1146-1156 (1998).
23. Saur et al., Gastroenterology 118, 849-858 (2000).
24. Saur et al., Am J Physiol Gastrointest Liver Physiol 282, G349-G358 (2002).
25. Putzke et al., Brain Res Mol Brain Res 85, 13-23 (2000)
26. Panda et al., J Biol chem, 278, 37122-37131 (2003).
27. Kone et al., Am J Physiol renal Physiol 285, F178-F190 (2003).
28. Watkins et al J Clin Invest 106, 803 (2000)
29. Wrzos et al Dig Dis Sci 42, 2106-2110 (1997).
30. Adeghate et al Cell Mol Life Sci 60, 1172-1179 (2003).
31. Belai et al., Gastroenterology 89, 967-976 (1987).
32. Belai et al., Gastroenterology 92, 730-734 (1987).
33. Burnstock et al Clin Sci (Lond), 75, 629-635 (1988).
34. Belai et al., Gastroenterology 98, 1427-1436 (1990).
35. Belai et al., Gastroenterology 95, 1234-1241 (1988).
36. Cellek S., Curr Pharm Des, 10, 3683-3695 (2004).
37. Cellek S., Diabetes, 54, 212-219 (2005).
38. Cellek S., Diabetes, 52, 2353-2362 (2003).
39. Buchan A. M. Digestion 46 Suppl 2, 142-147 (1990).
40. Di Giulio et al., J Neurosci Res 24, 355-361 (1989).
41. Jenkinson et al., Br J Pharmacol 116, 1535-1544 (1997).
42. Takahashi et al., Gastroenterology 113, 1535-1544 (1997).
43. James et al. Am J Physiol Gastrointest Liver Physiol 287, G612-619 (2004).
44. Tougas et al., Gut 33, 466-471 (1992).
45. Ishiguchi et al., Auton Neurosci 95, 112-120 (2002).
46. Cosentino et al., Cardiovasc Res 43, 274-278 (1999).
47. Goren et al., Biochemistry 35, 16735-16745 (1996).
48. Klatt et al., Embo J 14, 3687-3695 (1995).
49. Kobayashi et al., J Pharmacol exp Ther 256, 773-779 (1991).

50. Gross and Levi., J Biol Chem 267, 25722-25729 (1992).
51. Thony et al., Biochem J 347 pt 1, 1-16 (2000).
52. Kamada et al., Brain Res Mol Brain Res 142, 19-27 (2005)
53. Shang et al., Free Rad Biol Med 39, 1059-1074 (2005).
54. Pannirselvam et al., Br J Pharmacol 29, 8-15 (1997)
55. Cosentino et al., Circulation 91, 139-144 (1995).
56. Mitchell et al., Cardiovasc Pharmacol 43, 93-98 (2004)
57. Pieper M., J Cardiovasc Pharmacol 29, 8-15 (1997)
58. Cai et al., Cardiovasc Res 65, 838-849 (2005).
59. Cai et al., Diabetologia 48, 1933-1940 (2005).
60. Meininger et al., FASEB J 18, 1900-1902 (2004).
61. Alp et al., J clin Invest 112, 725-735 (2003).
62. Stroes et al., J Clin Invest 99, 41-46 (1997)
63. Maier et al., J Cardiovasc Pharmacol 35, 173-178 (2000)
64. Heitzer et al., Diabetologia 43, 1435-1438 (2000).
65. Heitzer et al., Circ Res 86, E36-E41 (2000).
66. Aytug et al., Am J Physiol Gastroenterol Liver Physiol 280, G255-G263 (2001).
67. Soffer et al., Am J Gastroenterol 93, 1318-1323 (1998).
68. Knight et al., Am J Gastroenterol 92, 968-975 (1997).
69. Chen et al., Am J Physiol 268, G171-G176 (1995)
70. Coskun et al., Res Exp Med (Berl) 195, 49-54 (1995).
71. Wang et al., World J Gastroenterol 9:775-8 (2003).
72. Resnick and Howard, Annu Rev Med 53:245-67 (2002).
73. Mankhey et al., Am J Physiol Renal Physiol 288:F399-405 (2005).
74. Leonelli et al., Neuroscience 144:1293-304 (2007).
75. Veiga et al., Neurosci Lett 402:150-3 (2006).
76. Caruso et al., Neurochem Int (2007).
77. Boonyaratanakornkit and Edwards, Semin Reprod Med 25:139-53 (2007).
78. Barros et al., Trends Mol Med 12:425-31 (2006).
79. Widder et al., Hypertension 42:991-6 (2003).
80. Cid et al., Ann N Y Acad Sci, 966:143-57 (2002).
81. Wen et al., Neuroreport 15:1515-8 (2004).
82. Murphy and Steenbergen Heart Fail Rev 2007.
83. Scordalakes et al., J Comp Neurol 453:336-44 (2002).
84. Garcia-Duran et al., Circ Res 85:1020-6 (1999).
85. Gingerich and Krukoff, Endocrinology 146:2933-41 (2005).
86. El-Sakka et al., Int J Impot Res 11:123-32 (1999).
87. Simoncini et al., Hum Reprod (2007).
88. Kawano et al., Histochem Cell Biol 121:399-405 (2004).
89. Campbell-Thompson et al., Endocrinol 171:65-73 (2001).
90. Serova et al., Neuroscience 140:1253-63 (2006).
91. Serova et al., Brain Res 1015:1-8 (2004).
92. Lam et al., Menopause 13:294-302 (2006).
93. Miyazaki-Akita et al., J Pharmacol Exp Ther 320:591-8 (2007).
94. Gangula et al., Am J Physiol Gastrointest Liver Physiol 292:G725-33 (2007).
95. Blades et al., Diabetologia 28:348-354 (1985).
96. Kirchick et al., Endocrinology 105:1343-1349 (1979.
97. Fiege et al., Mol Genetics and Metabolism 81:45-51 (2004).
98. Levy et al., Lancet 370(9586):504-510 (2007).
99. Gangula et al. Am J Physiol Gastrointest Liver Physiol 298: G692-G699 (2010).
100. Martinez et al., Am J Physiol Gastrointest Liver Physiol 274:G965-G970 (1998).
101. Nathan et al. *Cell* 78:915-18 (1994).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A method of treating gastroparesis in an individual, comprising:
    administering a pharmacologically effective amount of sepiapterin to an individual having gastroparesis.
2. The method of claim 1, wherein sepiapterin is administered in combination with other medications.
3. The method of claim 1, wherein the gastroparesis is diabetic gastroparesis.

* * * * *